United States Patent
Daly et al.

(10) Patent No.: US 11,638,835 B2
(45) Date of Patent: May 2, 2023

(54) SYSTEMS AND METHODS FOR AESTHETIC TREATMENT

(71) Applicant: Dominion Aesthetic Technologies, Inc., San Antonio, TX (US)

(72) Inventors: John G. Daly, San Antoinio, TX (US); Robert E. McKinney, San Antonio, TX (US); Scott R. Marable, San Antonio, TX (US); Matthew D. Hawk, San Antonio, TX (US)

(73) Assignee: Dominion Aesthetic Technologies, Inc., San Antonio, TX (US)

( * ) Notice: Subject to any disclaimer, the term of this patent is extended or adjusted under 35 U.S.C. 154(b) by 198 days.

(21) Appl. No.: 17/017,179

(22) Filed: Sep. 10, 2020

(65) Prior Publication Data
US 2020/0406055 A1    Dec. 31, 2020
US 2023/0093778 A9    Mar. 23, 2023

Related U.S. Application Data

(63) Continuation of application No. 15/820,737, filed on Nov. 22, 2017, now Pat. No. 10,994,151.
(Continued)

(51) Int. Cl.
*A61N 5/06*    (2006.01)
*A61B 18/20*    (2006.01)
(Continued)

(52) U.S. Cl.
CPC .......... *A61N 5/0616* (2013.01); *A61B 18/203* (2013.01); *A61B 18/22* (2013.01);
(Continued)

(58) Field of Classification Search
CPC .................. A61N 5/0616; A61N 5/067; A61N 2005/005; A61N 2005/007;
(Continued)

(56) References Cited

U.S. PATENT DOCUMENTS 5,878,144 A    3/1999    Aucsmith et al.
5,968,033 A    10/1999    Fuller et al.
(Continued)

FOREIGN PATENT DOCUMENTS

CA    2 646 881    *  9/2007    ............. A61B 18/18
DE    10307260 A1    8/2003
(Continued)

OTHER PUBLICATIONS

International Search Report in International Patent Application No. PCT/US2017/063010, dated Feb. 12, 2018.
(Continued)

*Primary Examiner* — Brian T Gedeon
(74) *Attorney, Agent, or Firm* — Greenberg Traurig, LLP; Chinh H. Pham; Jose R. Vento

(57) ABSTRACT

Provided herein is a multifunctional aesthetic system including a housing, an electromagnetic array situated in the housing and having a plurality of electromagnetic radiation (EMR) sources, each EMR source configured to generate an EMR beam having a wavelength different than that of an EMR beam generated by another of the EMR sources, a controller in electronic communication with the array to operate two or more of the EMR sources to direct the EMR beam to a treatment area, and a sensor in electronic communication with the controller for providing feedback to the controller based on defined parameters to allow the controller to adjust at least one operating condition of the multifunctional system in response to the feedback.

19 Claims, 20 Drawing Sheets

Related U.S. Application Data

(60) Provisional application No. 62/601,674, filed on Mar. 28, 2017, provisional application No. 62/497,535, filed on Nov. 22, 2016, provisional application No. 62/497,534, filed on Nov. 22, 2016, provisional application No. 62/497,520, filed on Nov. 22, 2016, provisional application No. 62/497,503, filed on Nov. 22, 2016.

(51) Int. Cl.
| | | |
|---|---|---|
| *A61B 18/22* | (2006.01) | |
| *G02B 3/08* | (2006.01) | |
| *G02B 27/09* | (2006.01) | |
| *G02B 27/10* | (2006.01) | |
| *A61N 5/00* | (2006.01) | |
| *A61B 18/00* | (2006.01) | |
| *A61N 5/067* | (2006.01) | |

(52) U.S. Cl.
CPC .......... *A61B 2018/00017* (2013.01); *A61B 2018/00023* (2013.01); *A61B 2018/00029* (2013.01); *A61B 2018/0047* (2013.01); *A61B 2018/00047* (2013.01); *A61B 2018/00202* (2013.01); *A61B 2018/00458* (2013.01); *A61B 2018/00464* (2013.01); *A61B 2018/00476* (2013.01); *A61B 2018/00642* (2013.01); *A61B 2018/00702* (2013.01); *A61B 2018/00708* (2013.01); *A61B 2018/00714* (2013.01); *A61B 2018/00738* (2013.01); *A61B 2018/00791* (2013.01); *A61B 2018/2035* (2013.01); *A61B 2018/2065* (2013.01); *A61B 2018/20351* (2017.05); *A61N 5/067* (2021.08); *A61N 2005/005* (2013.01); *A61N 2005/007* (2013.01); *A61N 2005/063* (2013.01); *A61N 2005/0626* (2013.01); *A61N 2005/0632* (2013.01); *A61N 2005/0659* (2013.01); *A61N 2005/0661* (2013.01); *A61N 2005/0662* (2013.01); *G02B 3/08* (2013.01); *G02B 27/0944* (2013.01); *G02B 27/106* (2013.01)

(58) Field of Classification Search
CPC ...... A61N 2005/0626; A61N 2005/063; A61N 2005/0632; A61N 2005/0659; A61N 2005/0661; A61N 2005/0662; A61N 2005/0643; A61B 18/203; A61B 18/22; A61B 2018/00017; A61B 2018/00023; A61B 2018/00029; A61B 2018/00047; A61B 2018/00202; A61B 2018/00458; A61B 2018/00464; A61B 2018/0047; A61B 2018/00476; A61B 2018/00642; A61B 2018/00702; A61B 2018/00708; A61B 2018/00714; A61B 2018/00738; A61B 2018/00791; A61B 2018/2035; A61B 2018/20351; A61B 2018/2065; A61B 18/18; A61B 90/04; A61B 2090/0481; G02B 3/08; G02B 27/0944; G02B 27/106; A61F 7/00; A61F 2007/0052; A61F 2007/0063

See application file for complete search history.

(56) References Cited

U.S. PATENT DOCUMENTS

| | | |
|---|---|---|
| 6,080,146 A | 6/2000 | Altshuler et al. |
| 6,106,516 A | 8/2000 | Massengill |
| 6,508,813 B1 | 1/2003 | Altshuler |
| 6,517,532 B1 | 2/2003 | Altshuler et al. |
| 6,652,512 B2 | 11/2003 | Ota |
| 6,653,618 B2 | 11/2003 | Zenzie |
| 6,663,620 B2 | 12/2003 | Altshuler et al. |
| 6,878,144 B2 | 4/2005 | Altshuler et al. |
| 6,974,451 B2 | 12/2005 | Altshuler et al. |
| 6,976,985 B2 | 12/2005 | Altshuler et al. |
| 6,997,923 B2 | 2/2006 | Anderson et al. |
| 7,090,670 B2 | 8/2006 | Sink |
| 7,276,058 B2 | 10/2007 | Altshuler et al. |
| 7,351,252 B2 | 4/2008 | Altshuler et al. |
| 7,540,869 B2 | 6/2009 | Altshuler et al. |
| 7,586,957 B2 | 9/2009 | Sierra et al. |
| 7,763,016 B2 | 7/2010 | Altshuler et al. |
| 7,856,985 B2 | 12/2010 | Mirkov et al. |
| 7,929,579 B2 | 4/2011 | Hohm et al. |
| 8,002,768 B1 | 8/2011 | Altshuler et al. |
| 8,317,779 B2 | 11/2012 | Mirkov et al. |
| 8,322,348 B2 | 12/2012 | Mirkov et al. |
| 8,328,794 B2 | 12/2012 | Altshuler et al. |
| 8,328,796 B2 | 12/2012 | Altshuler et al. |
| 8,540,869 B2 | 9/2013 | Zakarian et al. |
| 8,915,948 B2 | 12/2014 | Altshuler et al. |
| 9,028,536 B2 | 5/2015 | Sierra et al. |
| 9,884,204 B1 | 2/2018 | Dolleris et al. |
| 10,500,413 B2 | 12/2019 | Altshuler et al. |
| 10,556,123 B2 | 2/2020 | Altshuler et al. |
| 10,994,151 B2 | 5/2021 | Daly et al. |
| 2001/0053907 A1 | 12/2001 | Ota |
| 2003/0060810 A1 | 3/2003 | Syrowicz et al. |
| 2005/0137658 A1 | 6/2005 | Hennings |
| 2005/0154431 A1* | 7/2005 | Quistgaard ............ A61B 34/32 607/96 |
| 2006/0189976 A1 | 8/2006 | Kami et al. |
| 2006/0195166 A1 | 8/2006 | Minamoto et al. |
| 2006/0200116 A1 | 9/2006 | Ferren et al. |
| 2006/0271028 A1 | 11/2006 | Altshuler et al. |
| 2007/0185553 A1 | 8/2007 | Kennedy |
| 2007/0219605 A1 | 9/2007 | Yaroslavsky et al. |
| 2007/0282318 A1 | 12/2007 | Spooner et al. |
| 2008/0015555 A1 | 1/2008 | Manstein et al. |
| 2008/0071332 A1 | 3/2008 | Nelson et al. |
| 2009/0131922 A1 | 5/2009 | Dewey et al. |
| 2009/0182315 A1 | 7/2009 | Zigan et al. |
| 2009/0221999 A1* | 9/2009 | Shahidi ................. A61B 34/10 128/898 |
| 2010/0268220 A1 | 10/2010 | Johnson et al. |
| 2011/0060322 A1 | 3/2011 | Manstein |
| 2012/0029499 A1 | 2/2012 | Bernabei et al. |
| 2012/0116373 A1 | 5/2012 | Moench et al. |
| 2012/0150520 A1 | 6/2012 | Vaillant et al. |
| 2012/0232536 A1 | 9/2012 | Liu et al. |
| 2012/0239016 A1 | 9/2012 | Liu et al. |
| 2014/0025033 A1 | 1/2014 | Mirkov et al. |
| 2015/0265847 A1 | 9/2015 | Homer |
| 2015/0313532 A1 | 11/2015 | Marinkovich et al. |
| 2016/0166150 A1 | 6/2016 | Vilenskii |
| 2016/0270851 A1 | 9/2016 | Moench et al. |
| 2018/0140343 A1 | 5/2018 | Daly et al. |
| 2018/0140866 A1 | 5/2018 | Daly et al. |
| 2018/0303406 A1 | 10/2018 | McKinney et al. |
| 2018/0353772 A1 | 12/2018 | Chen et al. |
| 2020/0391051 A1 | 12/2020 | Daly et al. |

FOREIGN PATENT DOCUMENTS

| | | |
|---|---|---|
| JP | S56-124451 U | 9/1981 |
| JP | 2002-000745 A | 1/2002 |
| JP | 2008-518661 A | 6/2008 |
| JP | 2010-533569 A | 10/2010 |
| JP | 2011-515201 A | 5/2011 |
| WO | 1999027863 A1 | 6/1999 |
| WO | 2014149021 A2 | 9/2014 |
| WO | 2018226995 A1 | 12/2018 |

OTHER PUBLICATIONS

International Search Report in International Patent Application No. PCT/US2020/037550, dated Sep. 2, 2020.

(56) References Cited

OTHER PUBLICATIONS

AMS, "Color Sensors and Proximity Detection," 2012 (https://ams.com/documents/20143/36005/TCS3772_FS000111_1-00.pdf/ cAfe 790c-7faf-6b 1 f-3ae8-ada40622b2b6).

* cited by examiner

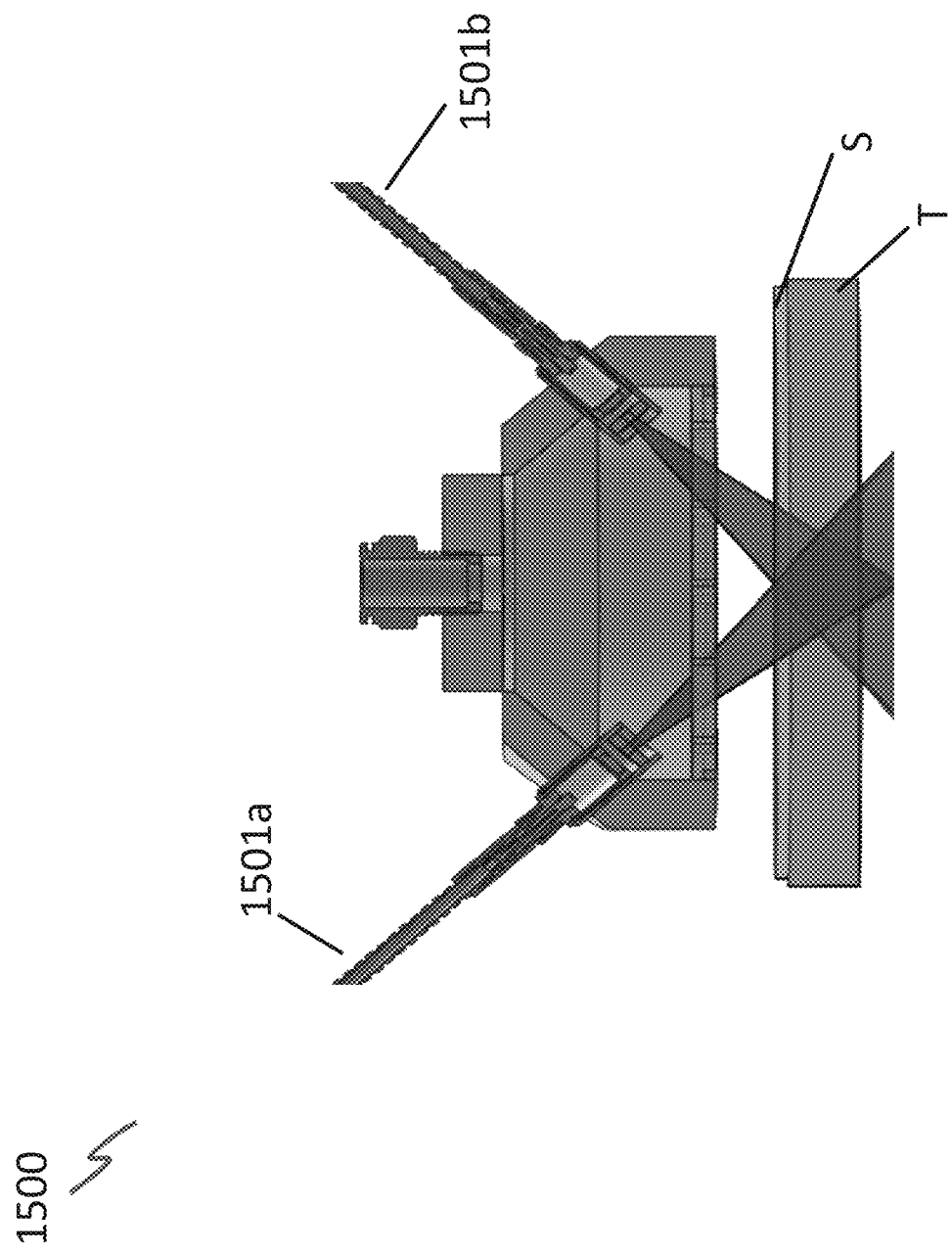

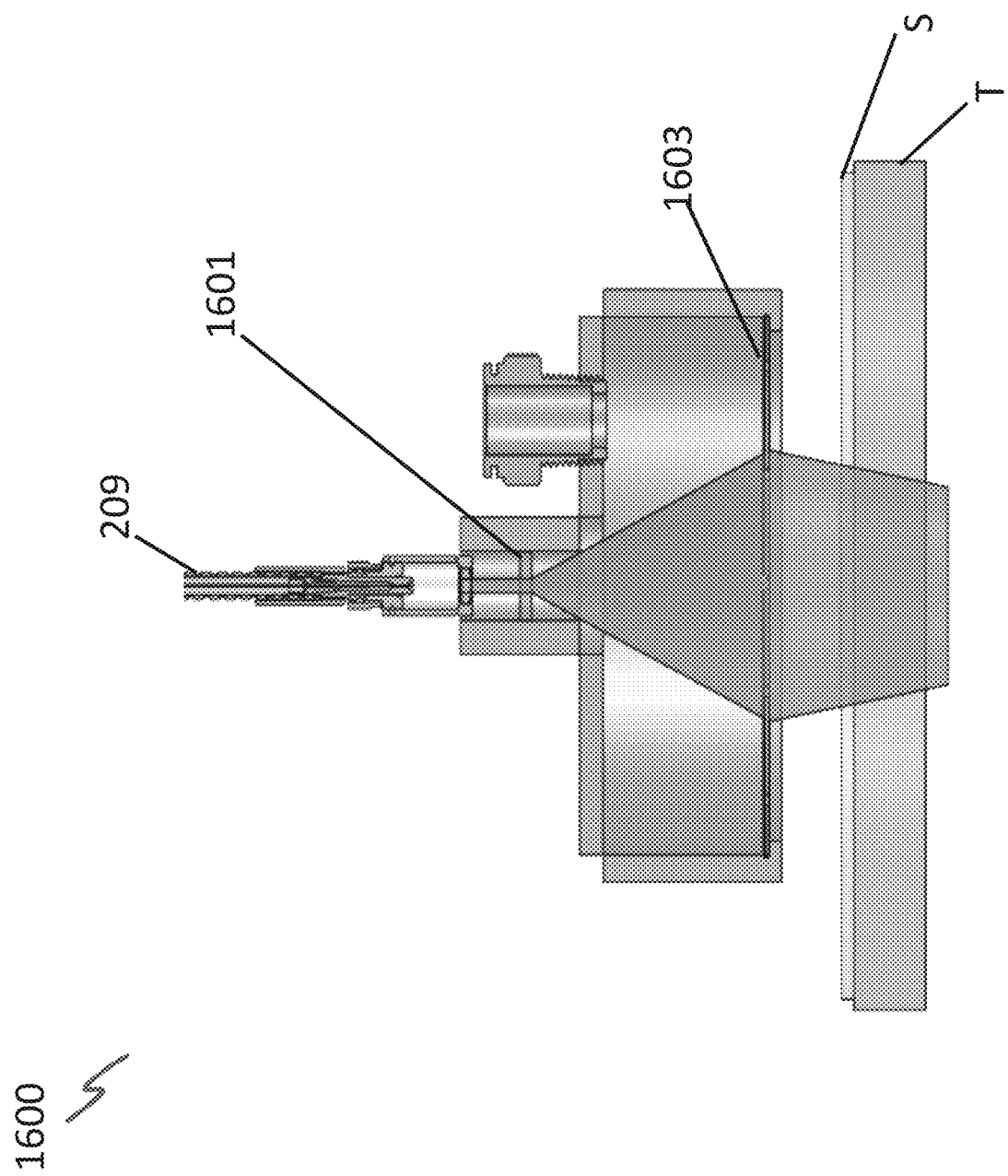

SYSTEMS AND METHODS FOR AESTHETIC TREATMENT

RELATED APPLICATIONS

This application is a continuation application of U.S. application Ser. No. 15/820,737, filed Nov. 22, 2017, which claims the benefit of and priority to U.S. Provisional Application No. 62/601,674, filed Mar. 28, 2017, which is hereby incorporated herein by reference in its entirety. This application also claims the benefit of and priority to U.S. Provisional Application No. 62/497,535, filed Nov. 22, 2016, which is hereby incorporated herein by reference in its entirety. This application also claims the benefit of and priority to U.S. Provisional Application No. 62/497,534, filed Nov. 22, 2016, which is hereby incorporated herein by reference in its entirety. This application also claims the benefit of and priority to U.S. Provisional Application No. 62/497,520, filed Nov. 22, 2016, which is hereby incorporated herein by reference in its entirety. This application also claims the benefit of and priority to U.S. Provisional Application No. 62/497,503, filed Nov. 22, 2016, which is hereby incorporated herein by reference in its entirety.

TECHNICAL FIELD

The present disclosure relates generally to aesthetic treatment systems, and more particularly, to multifunction aesthetic treatment systems.

BACKGROUND

Lasers have been applied to medical procedures since they became commercially available in the 1970's. Generally, aesthetic lasers are used for invasive, minimally invasive and non-invasive aesthetic procedures such as, for example, skin treatment and body sculpting. However, with a wide range of wavelengths and power levels, more than 50 different treatment protocols are common. Conventionally, a single laser system is packaged into a single medical device. Thus, conventionally, aesthetic practitioners may require many laser aesthetic treatment systems to perform various procedures. For example, some doctors may require 4, 5, 6, 7, 15, or more laser aesthetic systems to perform procedures requiring different treatment protocols such as, for example, skin ablation/peeling, wrinkle reduction, hyper pigmentation, rosacea, acne, mole removal, skin toning, vein treatments, body sculpting, hair removal, tattoo removal, etc.

Conventional aesthetic laser systems have low efficiency, requiring large power supplies and cooling systems. For example, some conventional laser aesthetic systems incorporate large flashlamp pumped lasers often weighing more than 100 lbs. Diode pumped solid state lasers are more efficient and somewhat smaller, but are expensive and have maintenance issues. Direct Diode lasers offer efficiency and potential low cost, but the need for high amperage power, cooling, and poor beam quality has limited their application.

SUMMARY

In one embodiment, a multifunctional aesthetic system is provided. The system includes a housing. The system also includes an electromagnetic array situated in the housing and having a plurality of electromagnetic radiation (EMR) sources, each EMR source configured to generate an EMR beam having a wavelength different than that of an EMR beam generated by another of the EMR sources. The system also includes a controller in electronic communication with the array to operate two or more of the EMR sources to direct the EMR beam to a treatment area. The system also includes a sensor in electronic communication with the controller for providing feedback to the controller based on defined parameters to allow the controller to adjust at least one operating condition of the multifunctional system in response to the feedback.

In some embodiments, the housing is designed to be portable. In some embodiments, the EMR sources are modularly replaceable within the array to provide customization of a combination of wavelengths generated by the EMR sources. In some embodiments, each EMR source is configured to generate an EMR beam having one of an infrared wavelength, a visible light wavelength, or an ultraviolet wavelength. In some embodiments, the controller is configured to operate the two or more EMR sources simultaneously, sequentially, or in an alternating pattern to emit the EMR beams from the two or more EMR sources. In some embodiments, the controller is configured adjust the at least one operating condition to maintain the treatment area at a therapeutically acceptable temperature. In some embodiments, the controller is configured to adjust at least one of a flow rate of a cooling airflow impinging on the treatment area, a temperature of the cooling airflow impinging on the treatment area, a spacing between the treatment area and a cooling apparatus directing the cooling airflow onto the treatment area, a power of the EMR beam, a scanning speed of the EMR beam relative to the treatment area, or combinations thereof. In some embodiments, the sensor includes a temperature sensor, the feedback including temperature data indicating a temperature of the treatment area, wherein the at least one adjusted operating condition is an emitted EMR beam power. In some embodiments, the sensor includes a temperature sensor, the feedback including temperature data indicating a temperature of the treatment area, wherein the at least one adjusted operating condition is a flow rate of a cooling airflow directed onto the treatment area. In some embodiments, the sensor includes a temperature sensor, the feedback including temperature data indicating a temperature of the treatment area, wherein the at least one adjusted operating condition is a spacing between the treatment area and a cooling apparatus directing a cooling airflow onto the treatment area. In some embodiments, the sensor is configured to provide the feedback without contacting the treatment area.

In some embodiments, the system also includes an EMR pathway directing the EMR to the treatment area. In some embodiments, the pathway also includes two or more optically separated output fibers to permit simultaneous illumination of the target area by two or more different wavelengths. In some embodiments, the system also includes a device optically engaged with the pathway for modifying the EMR beam received from the pathway to direct the EMR beam onto the treatment area. In some embodiments, the device also includes an optical element for expanding the EMR beam to direct the EMR beam onto an expanded treatment area. In some embodiments, the device also includes a Fresnel lens for focusing the expanded beam to prevent expansion of the EMR beam in a subsurface treatment region below the treatment area. In some embodiments, the device also includes a beam splitter optically engaged between the pathway and the device for generating a plurality of output beams, wherein the plurality of output beams are emitted by the device to impinge on the treatment area separately and to overlap at a predetermined distance below the treatment area to treat a subsurface treatment region. In some embodiments, the device is optically engaged with a plurality of optically separate portions of the EMR pathway for generating a plurality of output beams, wherein the plurality of output beams are emitted by the device to impinge on the treatment area separately and to overlap at a predetermined distance below the treatment area to treat a subsurface treatment region. In some embodiments, the array also includes at least two of the EMR sources each configured to generate an EMR beam having a same wavelength for being directed to the device by the optically separate portions of the pathway. In some embodiments, the device is engaged with the sensor for providing feedback associated with the treatment area. In some embodiments, the device is configured to direct a cooling airflow onto the treatment area without disrupting the EMR beam. In some embodiments, the device is configured to direct the EMR beam onto the treatment area, direct the cooling airflow onto the treatment area, and provide the sensor feedback associated with the treatment area without contacting the treatment area. In some embodiments, the system also includes an apparatus engaged at a first end with the housing and engaged at a second end with the device to position the device to direct the EMR beam onto the treatment area. In some embodiments, the apparatus also includes an articulable arm to position the device. In some embodiments, the apparatus is configured to receive a signal from the controller to instruct a movement of the apparatus to position the device with respect to the treatment area. In some embodiments, the apparatus is configured to receive the signal from the controller responsive to feedback received at the controller from the sensor, wherein the sensor includes a position sensor, the feedback including position data indicating a position of the device relative to the treatment area, wherein the at least one adjusted operating condition is a position of the device. In some embodiments, the system also includes a chiller for chilling at least one of the EMR sources or a cooling airflow during operation. In some embodiments, the system also includes a second chiller for chilling another of the at least one of the EMR sources or the cooling airflow during operation.

In another embodiment, a method for aesthetic treatment using a multifunctional system is provided. The method includes operating, by a controller in electronic communication with an electromagnetic array situated in a housing, two or more electromagnetic radiation (EMR) sources of the array to direct an EMR beam generated by each EMR source to a treatment area, each EMR source configured to generate an EMR beam having a wavelength different than that of an EMR beam generated by another of the EMR sources. The method also includes providing, by a sensor in electronic communication with the controller, feedback to the controller based on defined parameters. The method also includes adjusting, by the controller, at least one operating condition of the multifunctional system in response to the feedback.

In some embodiments, each EMR source is configured to generate an EMR beam having one of an infrared wavelength, a visible light wavelength, or an ultraviolet wavelength. In some embodiments, the step of operating further comprises operating the two or more EMR sources simultaneously, sequentially, or in an alternating pattern to emit the EMR beams from the two or more EMR sources to maintain a therapeutically acceptable temperature in the treatment area. In some embodiments, the step of adjusting further comprises maintaining the treatment area at a therapeutically acceptable temperature. In some embodiments, maintaining the treatment area at a therapeutically acceptable temperature includes adjusting at least one of a flow rate of a cooling airflow impinging on the treatment area, a temperature of the cooling airflow impinging on the treatment area, a spacing between the treatment area and a cooling apparatus directing the cooling airflow onto the treatment area, a power of the EMR beam, a scanning speed of the EMR beam relative to the treatment area, or combinations thereof.

In some embodiments, the method also includes directing the EMR beam along an EMR pathway onto the treatment area. In some embodiments, the method also includes modifying the EMR beam in a device optically engaged with the pathway to direct the EMR beam onto the treatment area. In some embodiments, the step of modifying also includes expanding, by an optical element of the device, the EMR beam to direct the EMR beam onto an expanded treatment area. In some embodiments, the step of modifying also includes focusing, by a Fresnel lens, the expanded beam to prevent expansion of the EMR beam in a subsurface treatment region below the treatment area. In some embodiments, the step of modifying also includes splitting, by a beam splitter optically engaged between the pathway and the device, the EMR beam to generate a plurality of output beams. In some embodiments, the step of modifying also includes emitting, by the device, the plurality of output beams to impinge on the treatment area separately and to overlap at a predetermined distance below the treatment area to treat a subsurface treatment region. In some embodiments, the step of modifying also includes optically engaging the device with a plurality of optically separate portions of the EMR pathway to generate a plurality of output beams. In some embodiments, the step of modifying also includes emitting, by the device, the plurality of output beams to impinge on the treatment area separately and to overlap at a predetermined distance below the treatment area to treat a subsurface treatment region.

In some embodiments, the method also includes directing, to the device by the optically separate portions of the pathway, at least two EMR beams having a same wavelength, wherein the array includes at least two EMR sources each configured to generate EMR beams having a same wavelength. In some embodiments, the method also includes directing, via the device, a cooling airflow onto the treatment area without disrupting the EMR beam. In some embodiments, the steps of directing, by the device, the EMR beam onto the treatment area, directing, via the device, the cooling airflow onto the treatment area, and providing, by the sensor, feedback to the controller are performed without contacting the device or the sensor with the treatment area. In some embodiments, the step of adjusting also includes controlling, by the controller, a movement of an apparatus engaged with the housing to position the EMR beam with respect to the treatment area. In some embodiments, the step of adjusting also includes moving the apparatus in response to the feedback to reposition EMR beam.

BRIEF DESCRIPTION OF THE DRAWINGS

Illustrative, non-limiting example embodiments will be more clearly understood from the following detailed description taken in conjunction with the accompanying drawings.

FIG. 15 is a cross-sectional view of a device having split, angled EMR beam delivery in accordance with an embodiment of the present invention.

FIG. 16B is a cross-sectional view of the device of FIG. 16A having an adjustable optical element in accordance with an embodiment of the present invention.

DETAILED DESCRIPTION

Figure 1:
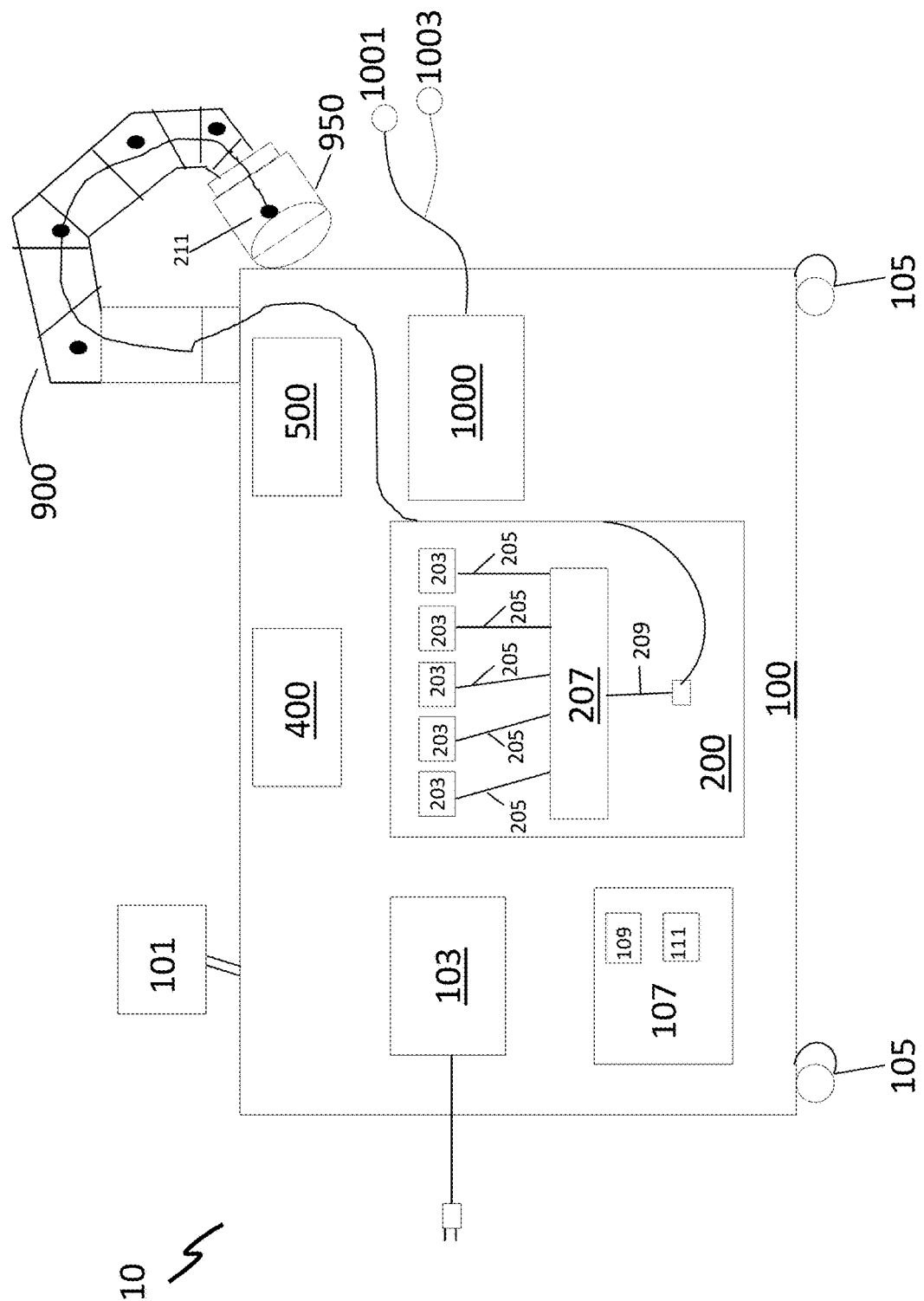
FIG. 1 is a block diagram illustrating a multifunction system in accordance with an embodiment of the present invention.

Various exemplary embodiments will be described more fully hereinafter with reference to the accompanying drawings, in which some example embodiments are shown. The present disclosure may, however, be embodied in many different forms and should not be construed as limited to the example embodiments set forth herein. Rather, these example embodiments are provided so that this disclosure will be thorough and complete, and will fully convey the scope of the present disclosure to those skilled in the art. In the drawings, the sizes and relative sizes of layers and regions may be exaggerated for clarity. Like numerals refer to like elements throughout.

Unless otherwise defined, all terms, including technical and scientific terms, used herein have the same meaning as commonly understood by one of ordinary skill in the art to which this disclosure belongs. For example, when an element is referred to as being "operatively engaged" with another element, the two elements are engaged in a manner that allows electrical and/or optical communication from one to the other.

Embodiments of the present disclosure generally provide multifunction aesthetic systems. In particular, in some embodiments, the systems of the present disclosure can include at least two electromagnetic radiation (EMR) sources and a beam combiner for combining electromagnetic radiation beams emitted by the at least two sources. In this manner, the multifunction aesthetic system can emit multiple wavelengths of electromagnetic radiation through a single output device. In some embodiments, the multiple wavelengths can be emitted simultaneously, in alternating pulses, and/or sequentially to permit multiple treatments to be performed by the same multifunction aesthetic system. In some embodiments, the multiple treatments can be performed sequentially, simultaneously, or in alternating fashion.

As used herein, EMR can refer to electromagnetic radiation having any desired wavelength. In particular, EMR generated and/or emitted by embodiments of the present disclosure can be any suitable wavelength, including, for example, visible light, ultraviolet radiation, x-ray radiation, infrared radiation, microwave radiation, radio waves, or combinations thereof.

Referring now to FIG. 1, a multifunction aesthetic system 10 can be provided for performing a variety of aesthetic procedures in a single medical device. The system 10 can include a housing 100 for housing, retaining, mounting, or engaging components of the system 10. In some embodiments, the housing 10 can be constructed of any suitable material for providing structural support to and protection of components housed, retained, mounted, or engaged in, on, or with the housing 100, including, for example, plastics, polymers, metals, or any other medically compliant material. To the extent that it is desired to move the system 10, for example, from one exam room or operating room to another, the housing 100 can include one or more wheels 105 to provide mobility of the system 10. To the extent that power is required to be delivered to the system 10, the housing 100 can include one or more power cords 103 for engagement with an AC power source such as, for example, a wall outlet.

In some embodiments, the system 10 can include a user interface 101 mounted to the housing 100 for receiving a user input. The user interface 101 can include, for example, an electronic display, a touch-screen monitor, a keyboard, a mouse, any other device or devices capable of receiving input from a user, or combinations thereof. The user input can include, for example, patient data such as height, weight, skin type, age, etc. as well as procedural parameters such as desired beam power, procedure type, wavelength or wavelengths to be applied, pulse duration, treatment duration, beam pattern, etc.

In some embodiments, the system 10 can also include a computing device 107 for receiving and storing the user input from the user interface 101, for storing and executing appropriate procedure protocols according to the user input, for providing control instruction to various components of the system 10, and receiving feedback from the various components of the system 10. The computing device 101 can be any suitable computing device such as, for example, a laptop, a desktop, a server, a smartphone, a tablet, a personal data assistant, or any other suitable computing device having a memory 109 and a processor 111. The memory 109, in some embodiments, can be any suitable memory 109 for storing electronic data, including the user input data and operational data associated with one or more components of the system 10. The memory 109 can include, for example, random access memory (RAM), flash memory, solid state memory, a hard disk, a non-transitory computer readable medium, any other form of electronic memory, or combinations thereof. The processor 111, in some embodiments, can be any processor suitable for receiving user input from the user interface 101, generating commands for operation of one or more system 10 components, executing any software stored in the memory 109, or combinations thereof. The processor, in some embodiments, can include one or more of a microprocessor, an integrated circuit, an application specific integrated circuit, a microcontroller, a field programmable gate array, any other suitable processing device, or combinations thereof.

Figure 2:
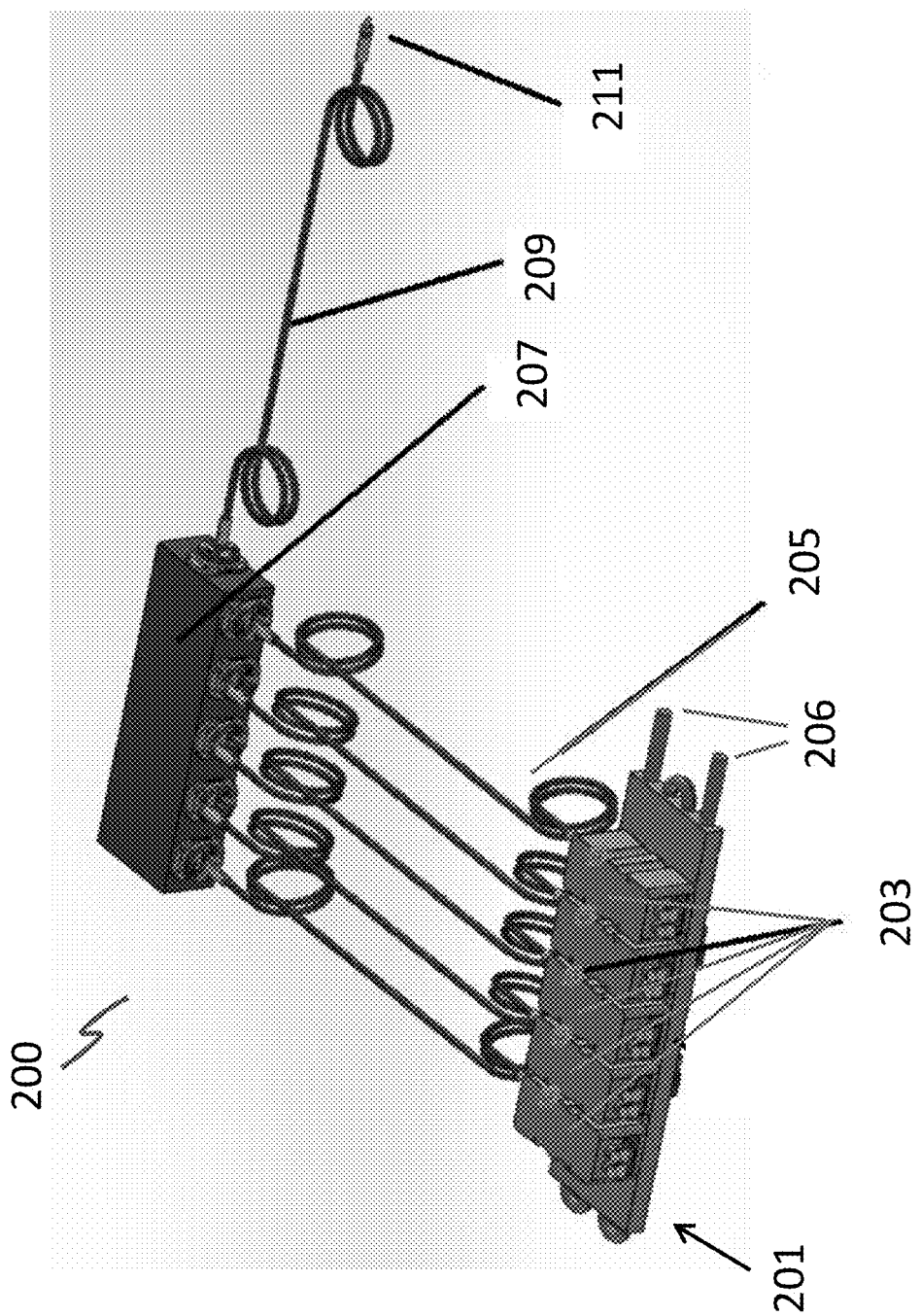
FIG. 2 is a perspective view of electromagnetic radiation emission components of a multifunction system in accordance with an embodiment of the present invention.

As shown in FIG. 1, the system 10 can also include an electromagnetic array 200. Referring now to FIG. 2, the electromagnetic array 200 can include a mount 201 for mounting a plurality of electromagnetic radiation (EMR) sources thereon. For example, as shown in FIG. 2, the mount 201 includes a plurality of laser sources 203 mounted thereon. The mount 201, in some embodiments, can include any plate, housing, bracket, or other structure for mounting one or more laser sources 203 thereto. As shown in FIG. 2, in some embodiments, the mount 201 can be a cold plate for providing cooling to the laser sources 203 mounted thereto. For example, as illustrated by FIG. 2, the mount 201 can provide first and second coolant ports 201a, 201b for permitting circulation of a coolant through the mount 201. The coolant can then chill the mount 201, thereby providing a heat sink for cooling the laser sources 203 mounted to the mount 201.

In some embodiments, each laser source 203 can be configured to emit EMR at a particular wavelength. For example, in some embodiments, each laser source 203 can emit EMR at a wavelength between about 200 nm to about 4500 nm. However, it will be apparent in view of this disclosure that each laser source 203 can emit EMR at any desired wavelength in accordance with various embodiments. Furthermore, it will be apparent in view of this disclosure that, in addition to laser sources 203, any other source of electromagnetic radiation having any wavelength can be used in accordance with various embodiments. For example, in some embodiments, EMR sources of the system 200 can emit electromagnetic radiation having any suitable wavelength, including, for example, visible light, ultraviolet radiation, x-ray radiation, infrared radiation, microwave radiation, or radio waves. Thus, because each laser source 203 can be configured to emit a different particular wavelength, just one system 10 can produce EMR beams at wavelengths or combinations of wavelengths required for any one of a plurality of procedures having disparate treatment protocol requirements. Accordingly, in some embodiments, the system can include laser sources 203 emitting wavelengths suitable for performing one or more procedures including, for example, but not limited to, fat reduction, body skin tightening, facial skin tightening, skin resurfacing, skin remodeling, vein reduction or removal, facial pigment removal or reduction, hair removal, acne treatment, scar reduction and removal, psoriasis treatment, stretch mark removal, nail fungus treatment, leukoderma treatment, tattoo removal, or combinations thereof.

Some aesthetic procedures may only require a single wavelength. For example, for some fat reduction procedures, a laser source 203 can be provided which is capable of emitting EMR at a wavelength of about 1064 nm (e.g., about 400 nm to about 3000 nm or about 900 nm to about 1100 nm) can be selected for hyperthermia of fat tissue because it exhibits good transmission through the skin, epidermis, and dermis and deposits energy within the fat cells. On the other hand, skin tightening generally requires other wavelengths that exhibit higher absorption in the epidermis and dermis, where the collagen resides. Thus, for example, a wavelength of about 1320 nm (e.g., about 400 nm to about 3000 nm or about 1300 nm to about 1500 nm) can be used for some body skin tightening procedures. These EMR beam wavelengths deposit more energy to the collagen, creating necrosis and eventually skin tightening from new collagen regrowth.

In other examples, such as for some facial pigment reduction or removal procedures and some vein reduction or removal procedures, for example, a laser source capable of emitting EMR at about 532 nm (e.g., about 500 nm to about 650 nm) can be provided.

Additionally, some aesthetic procedures or combinations of procedures may require two or more wavelengths. For example, to combine the fat reduction and body skin tightening procedures discussed above, a first laser source 203 capable of emitting EMR at 1064 nm and a second laser source 203 capable of emitting EMR at 1320 nm can be provided. In another example, for some facial skin tightening procedures, for example, a first laser source 203 capable of emitting EMR at about 1320 nm (e.g., 400 nm to about 3000 nm or about 1300 nm to about 1500 nm) and a second laser source 203 capable of emitting EMR at about 1470 nm (e.g., 400 nm to about 3000 nm or about 1300 nm to about 1500 nm) can be provided.

To provide additional functionality and facilitate ease of maintenance, in some embodiments, the laser sources 203 can be removably mounted to the mount 201 to permit modular replacement of the laser sources 203. Thus, in such modular configurations, individual laser sources 203 can be replaced, for example, to provide additional or different wavelengths or wavelength combinations as needed for particular procedures. However, it will be apparent in view of this disclosure that, in some embodiments, the laser sources 203 can be permanently attached to the mount 201.

The laser sources 203, in some embodiments, can include one or more fiber coupled lasers. For example, in accordance with various embodiments, the laser sources 203 can include one or more fiber coupled diode lasers and/or flashlamp or diode pumped lasers such as Er:YAG, Er,Cr:YSGG, Nd:YAG, Nd:glass; Er:glass, or any other suitable fiber coupled EMR source. In some embodiments, fiber coupled laser sources 203 can be rated as continuous wave (CW) devices operating at 50 W, 100 W, etc. Such CW devices can be operated in a gated mode where the pulse energy is equal to the pulse duration times the power. Therefore, a 100 W diode laser gated to operate for 5 milliseconds will have pulse energy of 500 mJ. In cases where more pulse energy is required but, for example, power supply or cooling capacity limits the average power, fiber coupled laser sources 203 can be configured as a quasi-CW device. Such quasi-CW devices can produce higher power pulses for the same average power draw by operating at a lower pulse frequency rate. In some embodiments, a quasi-CW device can produce pulses having up to 10 times the average power draw. Thus, for example, a 1000 W/100 W quasi-CW diode would be capable of pulsed operation at 5 milliseconds with 5 Joules per pulse, but limited to one tenth the pulse frequency of a CW laser.

In some embodiments, at least one of the laser sources 203 can include a fiber coupled diode laser. Such laser systems can advantageously operate at efficiencies exceeding 50%, are relatively small in size, draw relatively low power, and exhibit wide wavelength diversity. Fiber coupled diode lasers can, for example, be driven by less than 2.0 volts DC to produce an output of 10 kW or more. Furthermore, such laser sources 203 can be small and lightweight, with the module weighing about 500 grams per 1 kW. In one embodiment, at least one of the laser sources 203 can be a 75 W fiber coupled diode having a size of about 8×4×3 cm (less than 100 cm$^3$). In some embodiments, such laser sources 203 can be used to perform an aesthetic procedure while drawing less than 100 Watts of power. Such low power draw can, in some embodiments, reduce the amount of cooling required, permitting smaller, quieter, more efficient cooling systems.

The compliance voltage for nearly all diodes of interest is slightly less than 2.0 VDC. Packaging and differing bias voltage configurations can be applied to result in a common higher voltage which then allows a lower drive current. For example, a typical 50 W diode driven at 2.0 VDC can require a minimum threshold current of 8 amps to 12 amps and can require more than 60 to 70 amps to produce a desired power level. Such high current necessitates heavy gauge wiring such as #6 or #8 gauge wires to avoid voltage drop, preserve system reliability, and minimize Joule heating. To reduce the required current supply and wiring size, in some embodiments, the diode of each fiber coupled diode laser source 203 can be configured to operate with a common compliance voltage such as, for example, 20 VDC or 25 VDC, with a drive current controlled to match the laser selected and the required output power. By increasing the common compliance voltage to 20 or 25 VDC, the maximum drive current required to operate each laser source 203 can be limited to about 10 amps or less for most aesthetic procedures. By reducing required current, smaller gauge wiring can be used to improve reliability. In some embodiments, such an approach permits use of a single power supply to drive more than one of the laser sources 203 by manifolding the power supply into connections with multiple EMR sources. Thus, for example, in embodiments where only one laser is operated at a time, then the system 10 may be provided with only one power supply.

Typical diode packaging employs semiconductor bars with compliance voltages near 2.0 VDC, where threshold currents are in the 8 to 12 amperage range. To reach significant power levels, such diodes can operate as high as 70 amps. The associated problem with these voltage drops and joule heating ($I^2*R$) adds to reliability concerns. However, partial diode bars (i.e., diode bars having a shorter length than a standard 2.0 VDC diode bar) typically require less current proportional to the bar fraction. Thus, by using partial diode bars connected in series, delivering lower current but at a higher voltage for activating each of the partial diodes, required current can be reduced while power is maintained.

In some embodiments, at least one of the laser sources 203 can include a flashlamp or diode pumped laser. For example, many aesthetic skin treatments require application of EMR having a wavelength near 3000 nm, such as, for example, wavelengths greater than 2500 nm. Such wavelengths are typically produced by flashlamp or diode pumped solid state laser devices such as Er:YAG, which produces EMR having a wavelength of about 2940 nm or Er:YSGG, which produces EMR having a wavelength of about 2790 nm. However, although shown and described herein with reference to fiber coupled diode lasers and flashlamp or diode pumped lasers, it will be apparent in view of this disclosure that any suitable type of EMR source capable of being coupled to a fiber optic output cable can be used in accordance with various embodiments. In some embodiments, laser sources 203 including the flashlamp or diode pumped solid state laser devices can also be configured to operate at the common compliance voltage as explained above with reference to the fiber coupled diode lasers. Thus the system 10, in some embodiments, can use the common power source as discussed above with reference to the fiber coupled diode lasers.

Still referring to FIG. 2 the electromagnetic array 200 can also include a fiber optic relay cable 205 coupled to each laser source 203 for transmitting or relaying the EMR (also referred to as "EMR energy" or "beam") emitted by the respective laser source 203. In general, each fiber optic relay cable 205 can be constructed of any fiber optic material capable of transmitting EMR having a wavelength emitted by each respective laser source 203. In some embodiments, each fiber optic relay cable 205 can be constructed of, for example, low-OH silica fiber core cables, which transmit wavelengths in a range of about 200 nm to about 2400 nm, Zirconium Fluoride (ZrF4) and/or high purity Chalcogenide glass cables, which transmit wavelengths in a range of about 285 nm to about 4500 nm, or sapphire cables, which transmit wavelengths in a range of about 170 nm to about 5500 nm.

In some embodiments, the fiber optic relay cables 205 can be mated to the laser sources 203 by a fiber optic connector such as, for example, a SMA 905 connector or any other suitable connector. For each of the fiber optic relay cables, the fiber core diameter can be driven by the coupling efficiency of the diode driver and the required power. For example, in CW operation, in one embodiment, for near infrared wavelength ranges, the core diameter can be determined by an energy density limit in the cable of about 1.4 MW/cm$^2$ to provide a reliable relay. This reliability limit on the fiber predicts that a 100-micron core diameter can handle up to 85 W and a 400 micron core diameter can be used up to 1300 W. Shorter wavelengths typically scale to lower power limits. Additionally, for pulsed operation where the pulse duration is less than one (1) microsecond (1×10 seconds), fiber damage is not thermal but caused by dielectric breakdown and occurs at lower levels proportional to the pulse duration. That is, although average power is low enough to prevent overheating of the fiber, the power delivered during a pulse duration of less than one (1) microsecond can cause breakdown of the dielectric materials of the fiber. More generally, by selecting the proper fiber core diameter and connectors capable of handling maximum expected power loadings, safe and reliable routing of the EMR power generated by the laser sources 203 is possible.

Still referring to FIG. 2, the system can also include a beam combiner 207 for combining the EMR beams produced by each laser source 203 and transmitted by each relay cable 205 into a single output. Generally, the beam combiner 207 can be any device or system capable of combining several EMR beams of different wavelengths into one output. For example, in some embodiments, the beam combiner can include, for example, fiber switching devices, free-space fiber combiners, butt-coupled combiners, tapered fibers, bundled fibers, and fused fibers.

For example, free space combiners can be packaged with mirrors and gratings to fold separate beams into one fiber. Butt-coupled fiber combiners can mate smaller core fibers into a larger core output cable. For butt-coupled fiber combiners, the smaller fibers are stripped to their cladding and packaged as close to each other as possible, for example, in a circular footprint. The polished fiber ends can be mated (butt-coupled) to a larger fiber core with a diameter greater than the multiple fiber footprint. Tapered fibers can be used to reduce the core diameter of the combined fibers. That is, tapered fibers can be stretched such that the diameter of each tapered fiber is reduced to permit a higher packaging density for fiber coupling. Fiber fusing can be used to mate multiple fibers together by stripping the fibers and bundling them into a close-packed cross-section. The fibers can then be heated and melted to fuse into a single output fiber. Bundled fiber cables can also be used to route multiple sources into one output path. Bundled fibers, in general, can be larger diameter fiber cables formed from many small, individual fibers closely packed within the cable.

Figure 3:
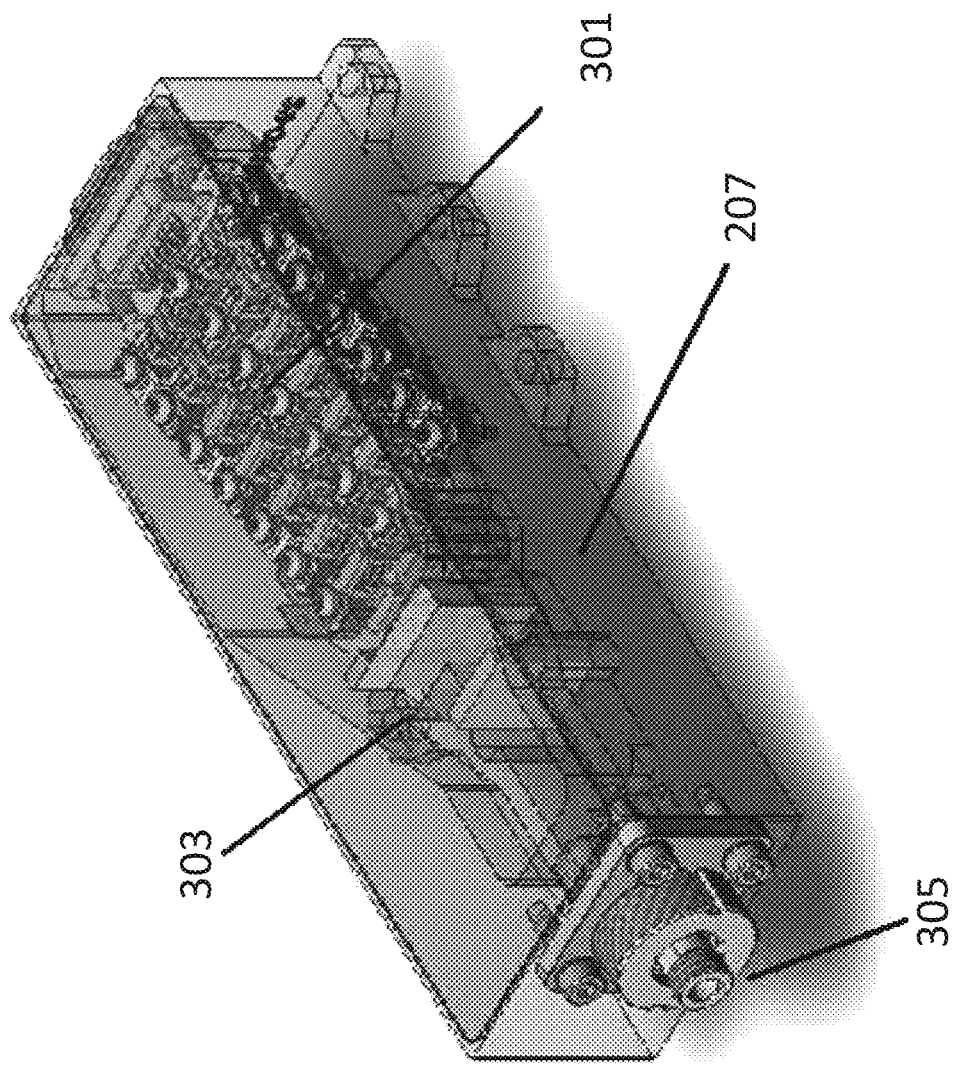
FIG. 3 is an interior view of a beam combiner of a multifunction system in accordance with an embodiment of the present invention.

Additionally, as shown in FIG. 3, in some embodiments, the beam combiner 207 can include a high brightness/low cost fiber coupling package such as the device produced for nLight Corporation under NASA SBIR program 05-II S6.02-8619. The device can include multiple diodes 301 all coupled into a single core fiber output port 305. The beam combining optics 303 can be configured to converge each of the individual diode 301 outputs into a common optical path. The beam combiner can then route the converged outputs to an output port 305 (e.g., a SMA 905 connector). The beam combiner 207, in some embodiments, can be configured to combine diverse beam wavelengths for beam powers ranging from a few Watts to more than 10 kW.

In such embodiments, because only the laser sources 203 producing the desired wavelengths are activated at any time, the beam combiner 207 can be a passive device, rather than an active fiber switch. Having a passive device also helps in defining the power limits for the fibers, where the limit in watts for the fibers can be matched to the highest power laser source 203 available where only a single laser source 203 is active at a time, rather than a sum from each laser source 203. To the extent that multiple laser sources 203 are activated simultaneously, the power limit of the combined fibers must be equivalent to at least the sum of the power required to operate each active laser source 203. Alternatively, in some embodiments, the beam combiner 207 can also include one or more fiber switches to selectively output particular wavelengths.

The beam combiner 207 can then output the combined beam to a common output cable 209 coupled to the beam combiner 207 for transmitting or relaying the EMR (also referred to as "treatment energy" or "beam") combined in the beam combiner 207. Advantageously, the common output cable 209 can permit the different beams produced by the laser sources 203 to be emitted through a single optical device. In particular, by combining or directing the beams in the beam combiner 207 to the common output cable 209, a single optical device of the system 10 can emit beams of different wavelengths simultaneously, sequentially, or in an alternating pulsed pattern. Thus, advantageously, in some embodiments, two or more treatment procedures can be performed simultaneously, contemporaneously, or immediately sequentially to improve patient outcomes and to reduce a number of patient follow up procedures.

In some embodiments, the fiber optic output cable 209 can be, but is not limited to, substantially similar to fiber optic relay cables 205. More generally, the fiber optic output cable 209 can be any fiber optic cable capable of transmitting the combined beam emitted by the beam combiner 207 to a fiber optic output. In accordance with various embodiments, the output cable 209 can be formed as a single fiber, can be formed as a plurality of smaller, bundled fibers, or can be formed as two or more closely packed individual fibers for separately transmitting two or more distinct beams having different wavelengths.

More generally, although the relay cables 205 and the output cable 209 are shown herein as being fiber optic cables, it will be apparent in view of this disclosure that any optical pathway capable of directing or transmitting EMR from one or more EMR sources to the beam combiner 207 and from the beam combiner 207 to the treatment area can be used in accordance with various embodiments. For example, in some embodiments, the pathways can be constructed of a series of mirrors for directing the EMR beams.

Figure 14A:
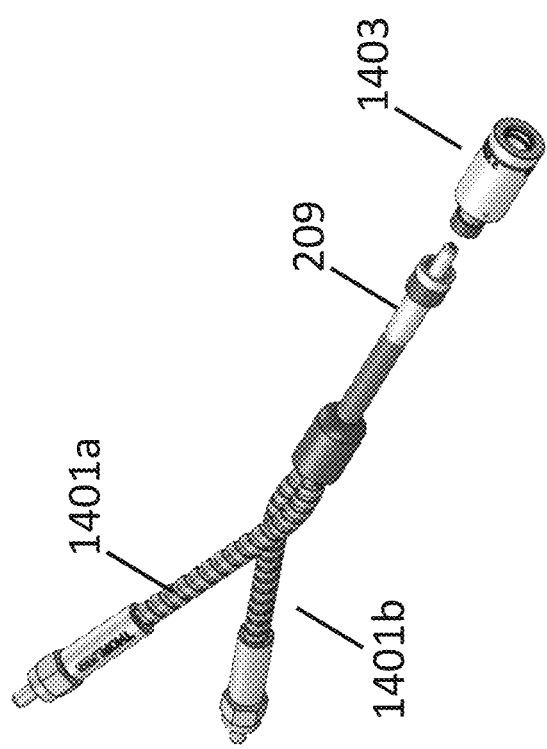
FIG. 14A is a perspective view of a fiber combiner for providing two separate output paths in accordance with an embodiment of the present invention.
Figure 14B:
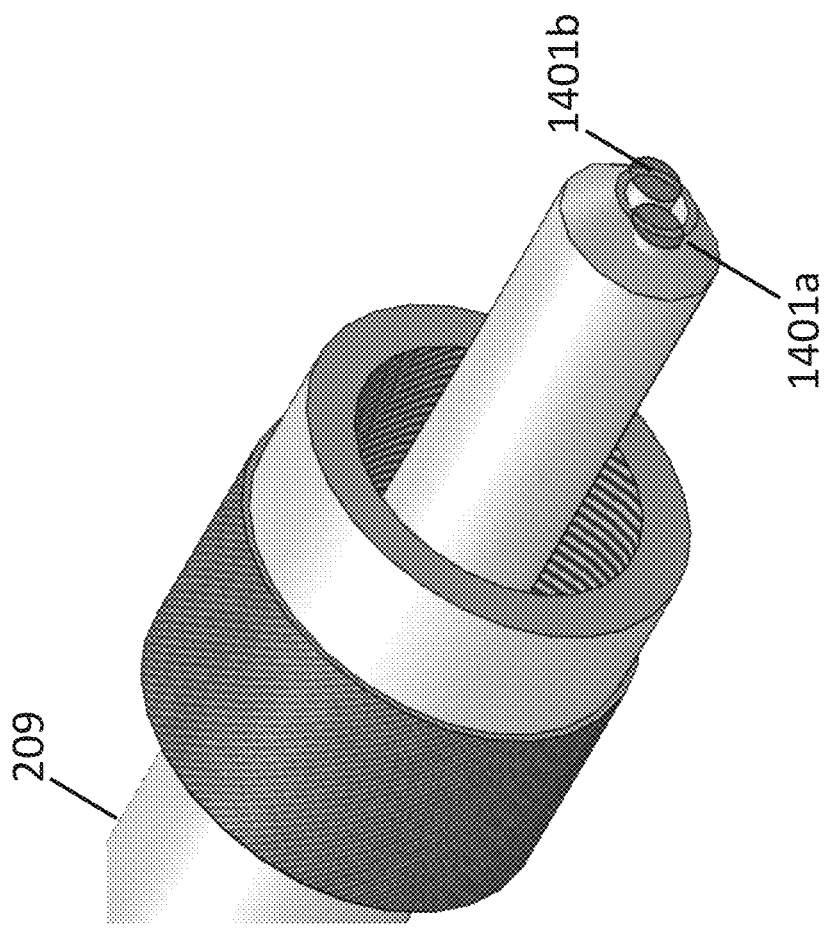
FIG. 14B is a detail view of the fiber combiner of FIG. 14A in accordance with an embodiment of the present invention.

For example, as shown in FIG. 14A, in order to route two separate beams from two distinct EMR sources to a single delivery device (e.g., a hand piece, robotic head, beam shaping optics) 1403, two individual fiber cores 1401a, 1401b can be combined to form a common output cable 209 to direct a beam from each active laser source 203 into a single output fiber connector 211. Referring now to FIG. 14B, because the fiber cores 1401a, 1401b of the common output cable 209 are adjacent and positioned near a center of an optical axis of one or more beam shaping components 1403, the beam shaping components 1403 can produce EMR beam outputs from either or both laser sources 203 with only a slight angular deviation from the true optical axis, the deviation having a negligible effect on beam shape and orientation.

In some embodiments, the fiber optic output cable 209 can also include a fitting 211 positioned at one end thereof for engagement with a device such as a hand piece, robotic head, or other emitter.

Figure 4:
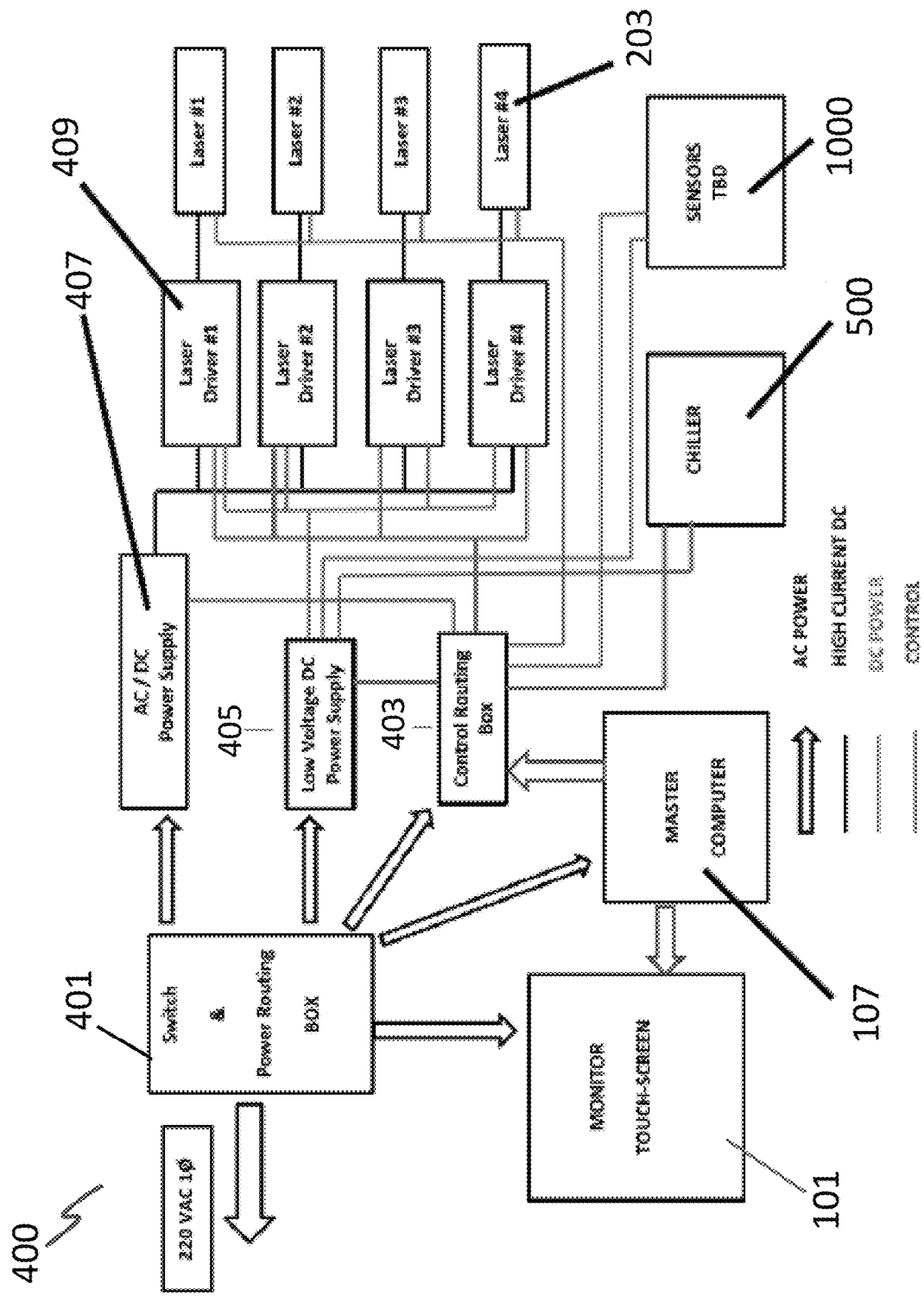
FIG. 4 is a schematic view of power and control electronics of a multifunction system including a plurality of EMR drivers in accordance with an embodiment of the present invention.

As shown in FIG. 1, in some embodiments, the system 10 can include power and control electronics 400 for powering and controlling various components of the system 10. Referring now to FIG. 4, in some embodiments, power and control electronics 400 can include a switch and power box 401 for receiving AC electrical power from the power cord 103 and distributing AC electrical power to various components as required for operation of the system 10.

The power and control electronics 400 can also include a controller 403, powered by the AC electrical power, in electronic communication with the computing device 107 to command one or more additional components of the system 400 to perform one or more directed operations to execute an aesthetic procedure.

The power and control electronics 400 can also include a low voltage ADC 405 for converting AC power from the power box 401 into low voltage DC power for operating one or more additional components of the power and control electronics 400. The low voltage ADC 405 can include any suitable ADC, including, for example, a direct conversion ADC, successive approximation ADC, ramp compare ADC, Wilkinson ADC, integrating ADC, delta encoded ADC, pipelined ADC, sigma delta ADC, time interleaved ADC, intermediate FM stage ADC, any other suitable ADC, or combinations thereof.

The system can also include a high voltage ADC 407 for converting AC power from the power box 401 into high voltage DC power for operating one or more additional components of the power and control electronics 400. The high voltage ADC 407 can include any suitable ADC, including, for example, a direct conversion ADC, successive approximation ADC, ramp compare ADC, Wilkinson ADC, integrating ADC, delta encoded ADC, pipelined ADC, sigma delta ADC, time interleaved ADC, intermediate FM stage ADC, any other suitable ADC, or combinations thereof.

The power and control electronics 400 can also include a plurality of diode drivers 409 for delivering drive current to the laser sources 203. The diode drivers 409, in some embodiments, can, for example, be semiconductor devices configured to pass a high current through a junction region between an n-type semiconductor and a p-type semiconductor. In such configurations, electrons produced by the n-type semiconductor in the presence of a current source such as DC power supply 407 can result in production of photons upon encountering holes of the p-type semiconductor. The photons can oscillate within the junction region, resulting in an optical gain in the junction region. When the current delivered to the semiconductor device exceeds a threshold current, the optical gain can exceed a threshold intensity, causing the photons to exit the junction region as a beam of laser light. In general, after reaching the threshold current, the laser output increases in power density (intensity) linearly in proportion to an increase in the input current. Furthermore, in some embodiments, the diode drivers 409 can also include regulators for controlling current input and one or more protective features such as, for example reverse current blocking and electrical spike suppression features.

In some embodiments, a single DC power supply 407 can be used for multiple diode drivers if the required compliance voltage for each driver 409/laser source 203 pair is the same and within the limits of the chosen diode driver. Sufficient current capability of the DC power supply 407 to operate the number of simultaneously driven driver 409/laser source 203 pairs is required. Advantageously, no special switching is required between the DC power supply 407 and the driver 409 or driver 409 and laser source 203. The DC power supply 407, in some embodiments, can be parallel connected to each driver 409. This presents an option for multiplexing the main power supply to the multiple laser sources 203.

In such embodiments, each of the diode drivers 409, when activated, can directly drive a single laser source 203 to produce a beam having a particular wavelength as discussed above with reference to FIG. 2. Thus, in some embodiments, one driver 409/laser source 203 pair can be activated for aesthetic procedures requiring a single wavelength EMR beam for treatment. Alternatively, in some embodiments, multiple driver 409/laser source 203 pairs can be activated any of simultaneously, sequentially, or in an alternating pulsed pattern to provide two or more wavelengths as required for a particular treatment and/or to combine or expedite treatments.

Referring again to FIG. 1, the system 10 can also include one or more cooling systems 500 for removing heat produced by the electromagnetic array 200 and the power and control electronics 400 and for delivering cold air for cooling of a patient's skin during a procedure. In general, cooling requirements are primarily dependent on heat generated by the electromagnetic array 200. For example, for a system operating a 100 W EMR source in a small package with an efficiency of about 50%, the cooling capacity can be as low as 200 watts.

Such heat is typically dissipated by one or more of forced air (e.g. fan) cooling, thermoelectric cooling, flowing coolant directly through the electromagnetic array 200, or a cooling plate. However, in general, forced air cooling is noisy and not efficient, thermoelectric coolers have relatively poor efficiency, requiring excessive heat dissipation at a heat sink. Other devices employ circulating coolant directly in the electromagnetic array 200, which can result in difficult maintenance and places a circulating fluid in close proximity to delicate optics, semiconductors, and high current. By contrast, baseplate cooling to cold plate is efficient, safe, quiet, and compact. Large cold plates can accommodate multiple EMR source heads and drive electronics. In some embodiments, several cold plates can be connected in series to the master circulating chiller. In some embodiments, one or more additional master circulating chillers can be provided as required to accommodate different cooling temperature requirements.

Figure 5:
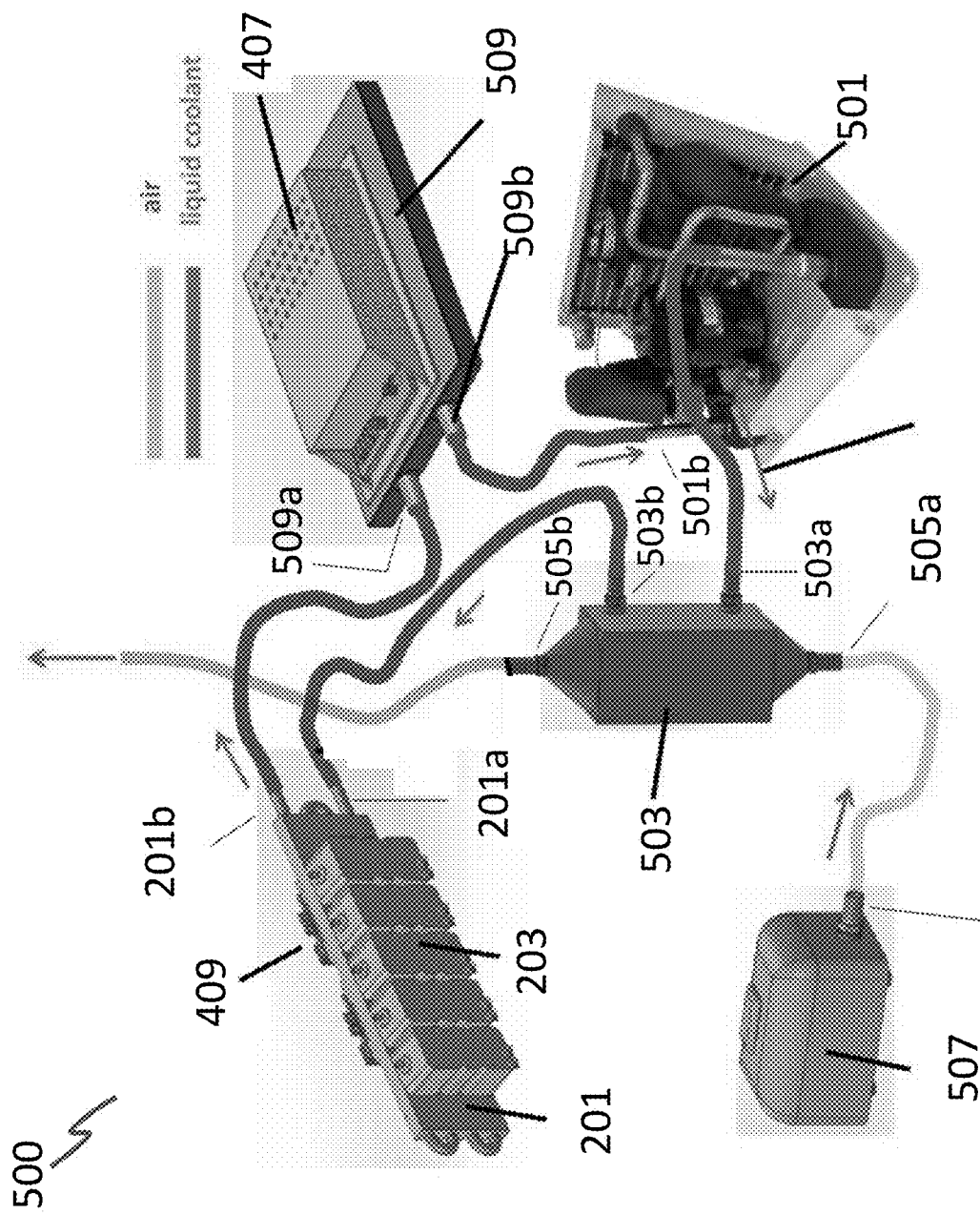
FIG. 5 is a perspective view of a cooling system of a multifunction system in accordance with an embodiment of the present invention.

As shown in FIG. 5, the cooling system 500 can include a refrigeration unit 501 such as a refrigerated heat exchanger, thermoelectric cooler, cold water heat exchanger, any other suitable cooling device, or combinations thereof. In some embodiments, a coolant output 501a can exit refrigerated coolant from the refrigeration unit 501. The coolant can then be routed through multiple devices to provide cooling and remove heat before being directed to a coolant return 501b for further refrigeration. Although shown having a single refrigeration unit 501 herein, it will be apparent in view of this disclosure that, in some embodiments, the cooling system 500 can include one or more additional independent refrigeration units 501 to cool various components at different temperatures. For example, in some embodiments, a first refrigeration unit can provide coolant at a temperature of about 0° C. to about 5° C. to chill cooling air for impingement on a patient during a procedure and a second refrigeration unit can provide coolant at a temperature of about 20° C. to about 25° C. to cool the electromagnetic array 200 without generating condensation, which could damage the laser sources 203. It will still further be apparent in view of this disclosure that, in some embodiments, the refrigeration unit 501 and/or the cooling system 500 can be provided with a temperature adjustment feature for permitting responsive adjustment of the coolant temperature depending on operational conditions and/or sensor feedback as needed to maintain therapeutically acceptable temperatures in the treatment area consistent with procedure requirements and to maintain operationally acceptable temperatures within the system 10 consistent with equipment requirements.

Figure 7:
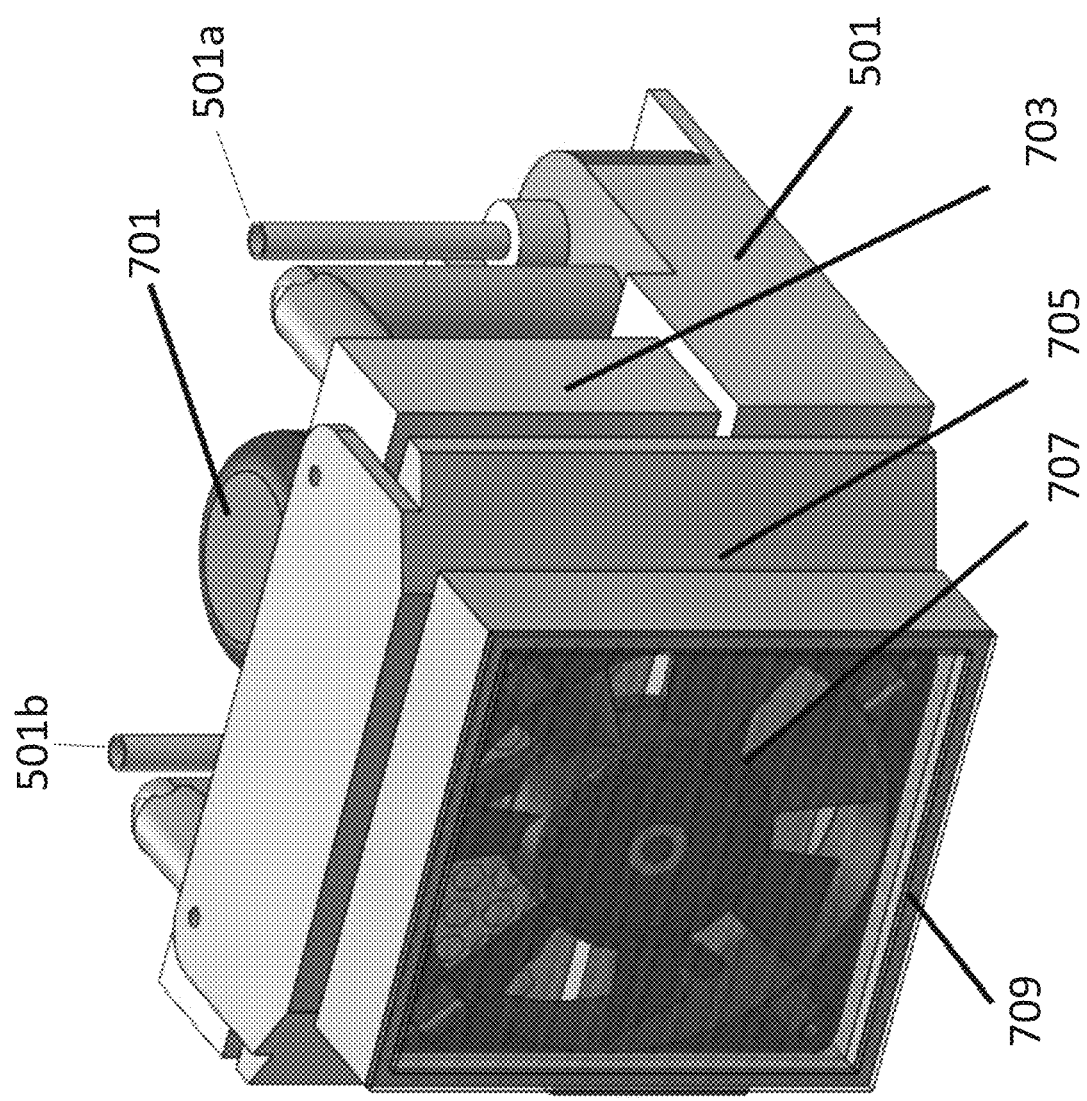
FIG. 7 is a perspective view of a refrigeration unit of a cooling system of a multifunction system in accordance with an embodiment of the present invention.

Referring now to FIG. 7, the refrigeration unit 501 can also include a compressor 701, a condenser 703, and an evaporator (not shown). The refrigeration unit 501 can provide forced convection cooling of the condenser 703 through a plenum 705 using a fan 707. In some embodiments, to improve air quality, the plenum 705 and fan 707 can include a HEPA filter 709 to capture particles, bacteria, and viruses, thereby preventing circulation of such particles, bacteria, and viruses through air surrounding the system 10.

In some embodiments, the coolant can be directed to a coolant inlet 503a of a heat exchanger 503, flowed through the heat exchanger 503, and exited from the heat exchanger 503 via coolant outlet 503b. The heat exchanger 503 can be any suitable device for cooling air or other gasses driven through the heat exchanger 503 via gas inlet 505a and exited via gas outlet 505b. The air or gas flowing in the heat exchanger 503, in some embodiments, can be used for cooling the skin of a patient during a procedure. For example, in some embodiments, the air or gas can cool the patient skin to a target temperature in the range of 15 to 20° C. via a gas impingement cooling of the skin during the procedure in order to maintain a therapeutically acceptable temperature range.

In some embodiments, the air or gas can be driven through the heat exchanger 503 by a pump 507. The pump 507, in some embodiments, can be any suitable device capable of driving the gas through the heat exchanger 503 and onward to a jet impingement nozzle (not shown). In some embodiments, in order to maintain a therapeutically acceptable temperature at the treatment area (e.g., a patient's skin), the pump 507 can be in electronic communication with the controller 403 to receive instructions from the controller for adjusting a flow rate of the cooling air or gas responsive to feedback from one or more temperature sensors monitoring the treatment area.

Figure 6:
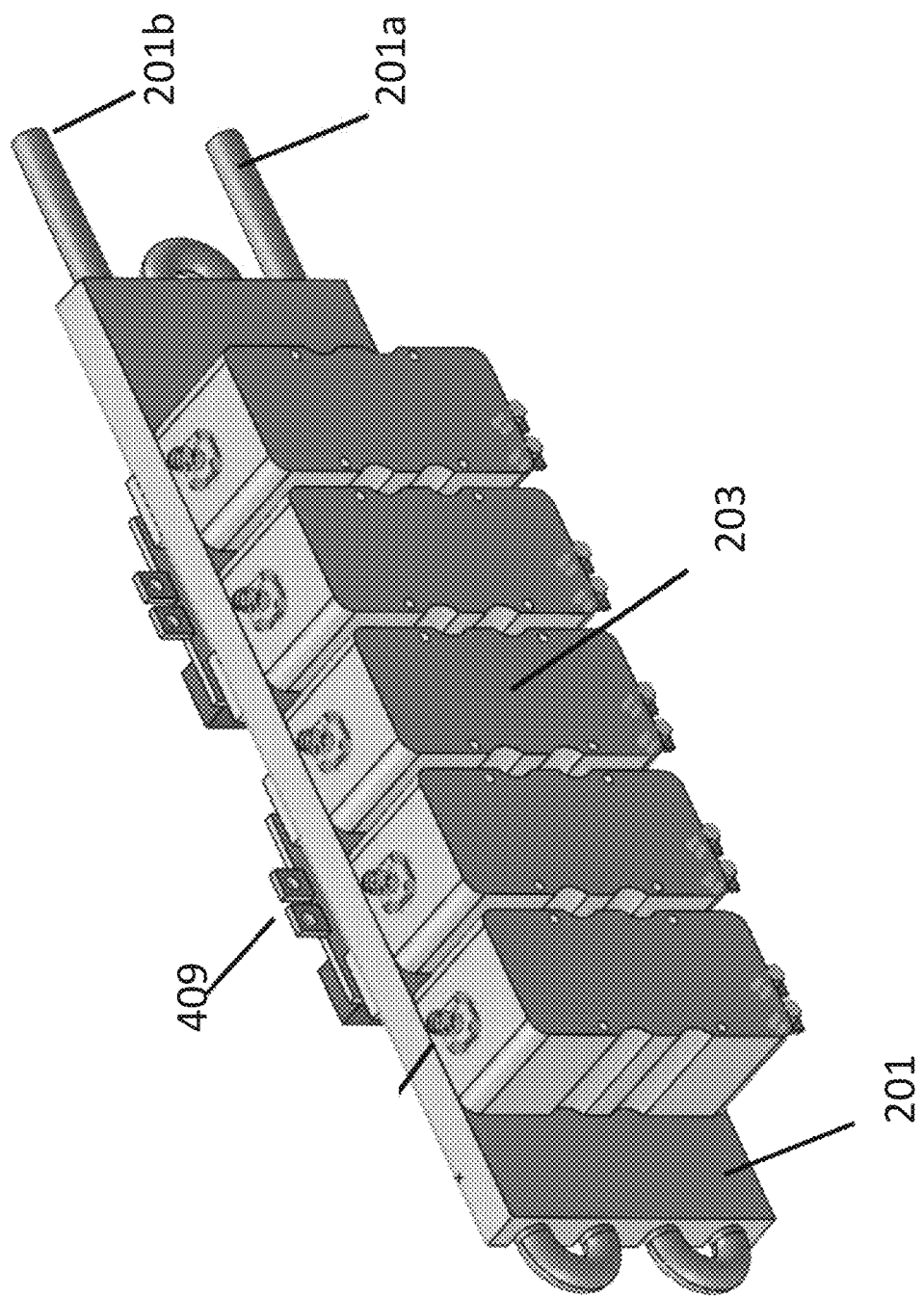
FIG. 6 is a perspective view of a cooling mount of a multifunction system in accordance with an embodiment of the present invention.

The cooling system 500, in some embodiments, can also route the coolant from the coolant outlet 503b of the heat exchanger 503 to a first coolant port 201a of a mount 201 as described above with reference to FIG. 2. The coolant can chill the mount 201, thereby providing a heat sink for cooling the laser sources 203 mounted to the mount 201. As shown with greater detail in FIG. 6, in some embodiments, the mount 201 can be a cold plate for cooling the laser sources 203 mounted thereto. In some embodiments, the mount 201 can also include one or more of the diode drivers 409 mounted thereto. In such embodiments, the cold plate mount 201 can advantageously cool both the diode drivers 409 and the laser sources 203 with a single cooling mechanism. Although the mount 201 cooling plate is shown herein as being sized for five laser sources 203 and two diode drivers 409, it will be apparent in view of this disclosure that the mount 201 can be sized to accommodate any number or combination of laser sources 203 and diode drivers 409.

Referring again to FIG. 5, the coolant can be exited from the mount 201 via a second coolant port 201b and routed to a coolant input 509a of a baseplate 509 of the DC power supply 407 to provide cooling to the DC power supply 407. The coolant can be exited from the baseplate 509 via a coolant output 509b of the baseplate 509 and routed to the coolant return 501b of the refrigeration unit 501.

Referring again to FIG. 1, the system 10 can also include one or more positioning apparatus 900 in accordance with various embodiments for permitting movement, control, and positioning of a device 950 coupled to the common output cable 209. In general, aesthetic EMR devices apply EMR energy with stationary or manually manipulated devices. Thus, the application of the heat energy is typically limited to small fixed areas in the case of stationary devices or, in the case of manually manipulated devices, a relatively uncontrolled and nonuniform dosage of total energy. Accordingly, in some embodiments, the positioning apparatus 900 can provide a multi-axis, computer controlled mechanism for controlled movement, orientation, and positioning of the device 950 used for emitting the EMR beams for treatment. In some embodiments, such positioning apparatus 900 can provide movement over a predefined treatment zone. In some embodiments, the computer control provides improved control and movement over stationary or manually operated systems. In particular, computer control can provide for scanning the device 950 across large areas during treatment to provide uniform heating of the target treatment area. Furthermore, the treatment pattern can be modified to any shape desired for treatment. For example, treatment patterns can be programmed to avoid existing scar tissue or the belly button area, where no target fat exists.

Figure 8:
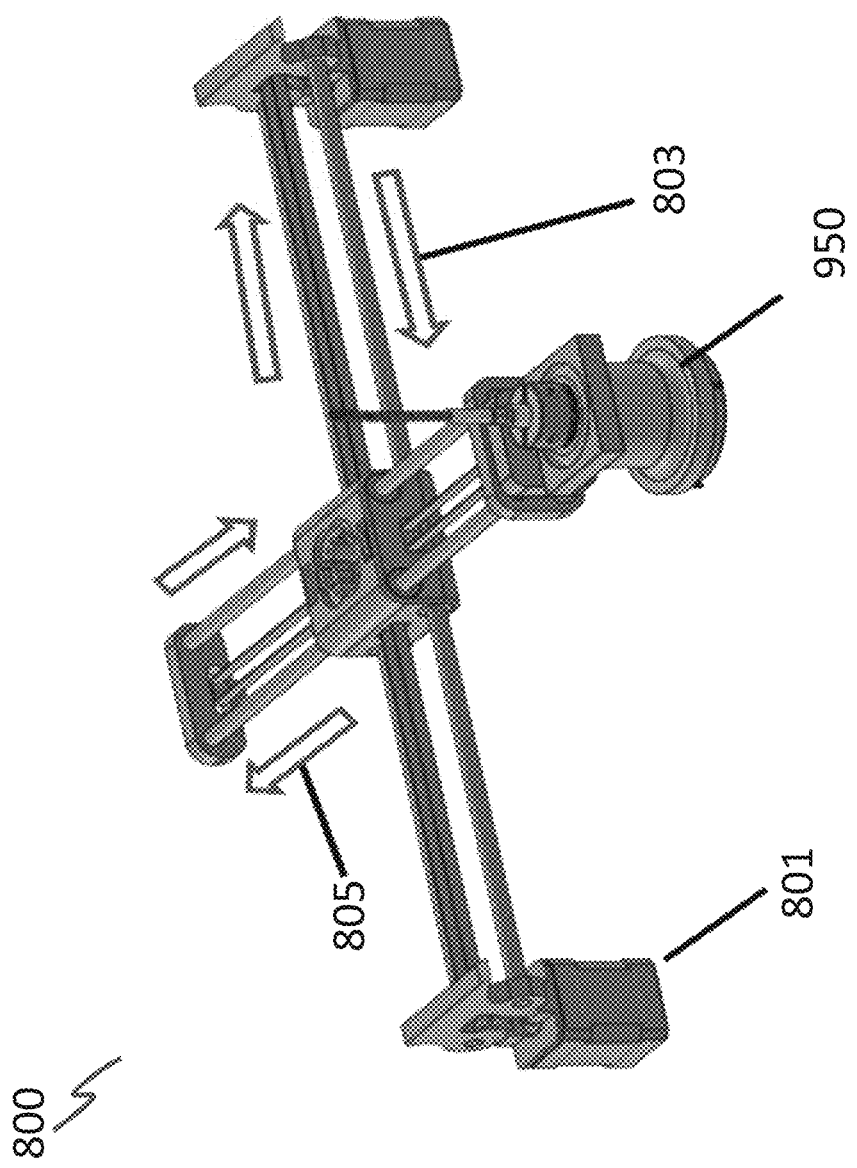
FIG. 8 is a perspective view of a two degree of freedom positioning apparatus in accordance with an embodiment of the present invention.

In order to provide desired coverage of an area to be treated and permit proper positioning of the device 950, the positioning apparatus 900 can be provided with any number of degrees of freedom for movement of the device 950. For example, in some cases a treatment process can employ only one DOF and move the device 950 back and forth over the treatment area. As shown in FIG. 8, in some embodiments having a substantially planar target treatment area, the positioning apparatus can be a two degree of freedom control device 800 having a first rail 803 for providing movement along an x-axis of the device 800 and a second rail 805 for providing movement along a y-axis of the device 800.

Figure 9:
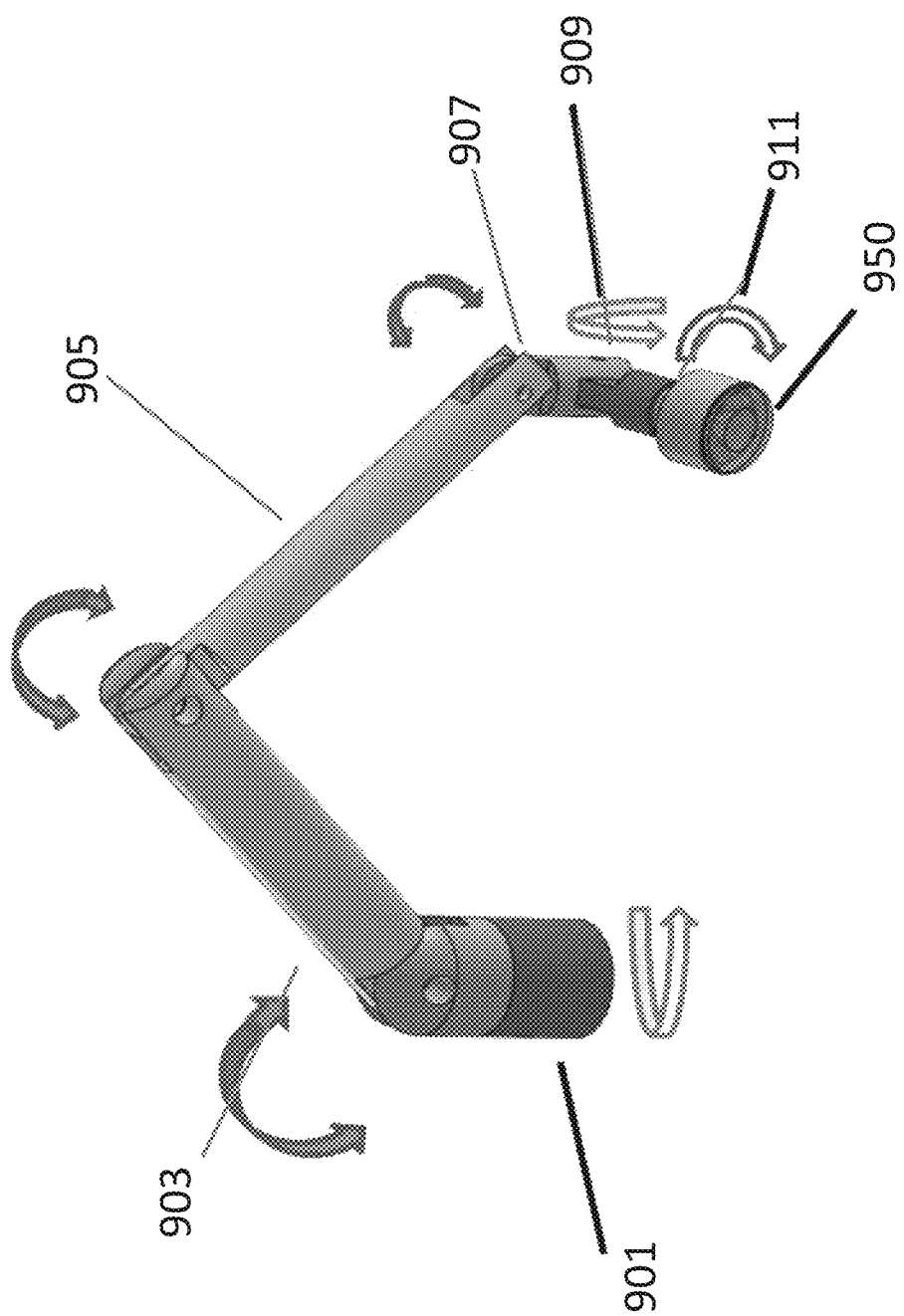
FIG. 9 is a perspective view of a six degree of freedom positioning apparatus in accordance with an embodiment of the present invention.
Figure 10:
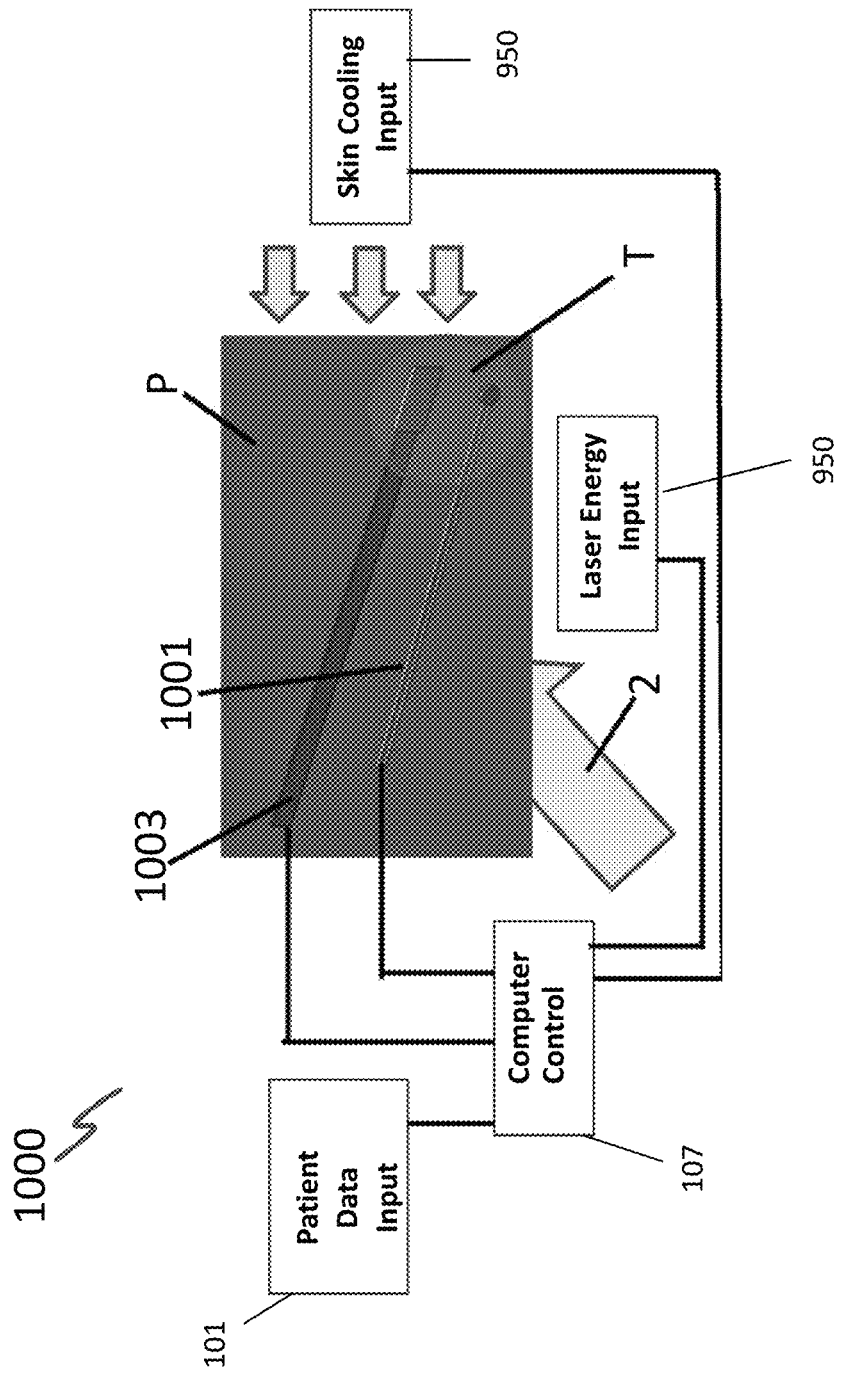
FIG. 10 is a schematic view of a subcutaneous temperature prediction system in accordance with an embodiment of the present invention.

Referring now to FIG. 9, in some embodiments, the positioning apparatus 900 can be a six degree of freedom robotic arm. The positioning apparatus 900 can include, for example, a rotatable base 901 providing a first degree of freedom of rotation of the positioning apparatus 900. The rotatable base 901 can be pivotably engaged with a first segment 903 to provide a second degree of freedom. The first segment 903 can be pivotably engaged with a second segment 905 to provide a third degree of freedom. The second segment 905 can be pivotably engaged with a third segment 907 to provide a fourth degree of freedom. The third segment 907 can be pivotably engaged with a fourth segment 909 to provide a fifth degree of freedom. The fourth segment 909 includes a rotatable portion 911 for rotating the device 950. In general, the rotatable base 901 can be engaged with the housing 100 of the system 10 or can be attached to a separate platform for positioning nearer the target treatment area. The six degrees of freedom of the positioning apparatus 900 can advantageously be used to follow the targeted patient's body shape and match the treatment zone desired.

Such positioning apparatus 900 can be important in various procedures such as, for example, in the case of subcutaneous fat reduction, where deposition of heat into the subcutaneous fat requires reaching and maintaining a therapeutically acceptable temperature range such as, for example, about 40° C. to about 48° C. over a period of time. In particular, in some embodiments, lower temperatures have no fat reduction benefit and higher temperatures can cause severe necrosis, cell damage, and scarring. Conventional devices modulate or cycle the power off and on to maintain this temperature range. However, the low thermal conductivity of fat makes EMR source on/off cycle times compatible with a scanning or moving the device during treatment to cover larger treatment areas and to avoid overheating of the treated tissue. Thus, the positioning apparatus 900 can be programmed to control the device 950 to follow the targeted patient's body shape and match the treatment zone desired. In such embodiments, the heat energy delivered, the treatment area, the dwell time for energy on and the heat source return time to maintain the target temperature are factors that can be used to determine the overall treatment protocol. Patient information, sensors, and feedback can also all be used to maintain a uniform heating over the entire treatment site by scanning the energy delivery module in such a fashion as to cover the entire site. However, it will be apparent in view of this disclosure that, in some embodiments, the system 10 may not include a positioning apparatus 900 and that the device 950 can instead be connected to the housing by the fiber output 209 and/or a cooling air source for manual operation and positioning. It will still further be apparent in view of this disclosure that, in some embodiments, the system 10 may include both a device 950 for use with the positioning apparatus 900 and a manually operated and positioned device 950 for use as required by a particular procedure. For example, the manually operated and positioned device 950 can be used where desired.

Furthermore, sensors 1000 and corresponding sensor feedback can be monitored in real time by the computing device 107 to permit the computing device 107 to reactively instruct (e.g., via controller 403) the positioning apparatus 900 to reposition the device 950. For example, in some embodiments, if the sensors 1000 detect that skin temperature is too high, the computing system 107 can instruct the positioning apparatus 900 to move the device 950 to a new location and/or to scan faster during treatment to reduce dwell time in one area and prevent overheating. In some embodiments, the if the sensors 1000 detect that skin temperature is too low, the computing system 107 can instruct the positioning apparatus 900 to increase a distance or spacing between the device 950 and the target surface to reduce the effects of cooling air flowing through the device 950. Still further, sensors 1000 can be included to detect a position of the device 950 relative to the surface to be treated. In such embodiments, the positioning apparatus 900 can responsively adjust a position or orientation of the device 950 relative to the surface to be treated according to the sensor 1000 feedback. For example, in some embodiments, the positioning apparatus 900 can maintain a prescribed separation height between the device 950 and the surface to be treated.

Numerical simulation modeling for an EMR source in the near-infrared where transmission to the subcutaneous fat is achieved shows that for 1.5 watts per centimeter squared over a 2×2 inch area, the adipose tissue at 12 mm depth reaches 47° C. within 50 seconds. This sample model also included controlled cooling of the skin at 30° C. Simulations show that, without cooling the skin surface would reach an unacceptable temperature of more than 57° C. In this case, the model also shows how the adipose tissue's temperature will decay with time. This model indicates that the patient can be treated in one zone for 50 seconds, after which the robotic control moves the energy source to the next zone for another 50 seconds. This can be repeated to multiple zones, only requiring return to the initial zone before its temperature falls too far below the target temperature range of 40 to 48° C. for efficient hyperthermia apoptosis. Additional modeling studies show that the second treatment duration requires less time to reach the 48° C. temperature and that the reduction in required reheat time is asymptotic.

It is important to note that this model is an example based on defined tissue characteristics. However, dwell times and reheat cycles may need to be adjusted on a case by case basis based on, for example, patient skin type, patient characteristics, wavelength, cooling characteristics, etc. Additionally, it will be apparent in view of this disclosure that the treatment does not need to target 48° C. and can instead target a lower temperature within a procedure-specific range. For example, the treatment can be successful with lower target temperatures, such as 44° C. In each case, the patient type and treatment time can be adjusted to a range of target temperatures. Additionally, it will be apparent in view of this disclosure that, in some embodiments, the temperature can be permitted to fall below the minimum effective temperature of 40° C. for short periods of time with reheating applied to raise the temperature back into the hyperthermia apoptosis targeted range. The application of computer control with the appropriate input parameters allows an efficient and optimized treatment protocol.

A pattern may be scanned in which the energy source returns to the initial treatment site in a time equal to the expected decay time of the temperature. Since reheating to the target temperature requires less time on the second pass, the energy source may be moved at a faster rate on the second pass over tissues. Energy source scanning patterns may be optimized for treatment of a maximum area in a minimum time, and will depend upon patient anatomy and tissue parameters. Scan rates and treatment patterns may be modified in real time based upon measured skin temperatures and heat flux and predicted subcutaneous tissue temperature. Energy source power may be modulated during movement of the energy source to further optimize treatment.

Referring again to FIG. 1, the device 950, in some embodiments, can be configured to emit the combined beam emitted by the beam combiner 207 and received via the fiber output 209 for treatment of the patient. In some embodiments, one or more devices 950 can be interchangeably engageable with the fitting 211 of the fiber optic output cable 209. In general, the device 950 can include mirrors, beam shaping optics or any other appropriate optical elements. For example, the fiber output can be emitted directly on the patient or mated to a collimating device. In a similar fashion, two or more EMR beams can be combined in free space using mirrors and beam splitting optics. The desired beam shape or pattern on the patient can be modified with an optical element, which can be a lens, lens array, a diffractive beam shaper, or any engineered diffusing device. The resulting beam shape can match the desired treatment pattern. In some embodiments, the output beam can be adjusted to match the desired beam diameter, power level, and be collimated, diverging, or converging. As stated above, one or more of the laser sources 203 can be operated simultaneously, alternately, or in sequences. This can be controlled by the input to each laser source 203 since the fiber cables and routing optics are passive devices. EMR beam switches or interlocks can be included as required for safety and regulation compliance. In some embodiments, the device 950 can also include a distance sensor for providing feedback to the computer 107 for adjusting positioning by the positioning apparatus 900.

Additionally, although shown in FIG. 1 and described herein as being mounted and/or coupled to the positioning apparatus 900, it will be apparent in view of this disclosure that, in some embodiments, the device 950 may, in some embodiments, be used as a manual hand piece. In such embodiments, the device 950 may not be coupled to any positioning apparatus and instead can be coupled to the housing 100 only by the fiber output 209 and/or a cooling air supply for permitting manual operation and positioning of the device 950.

Figure 17:
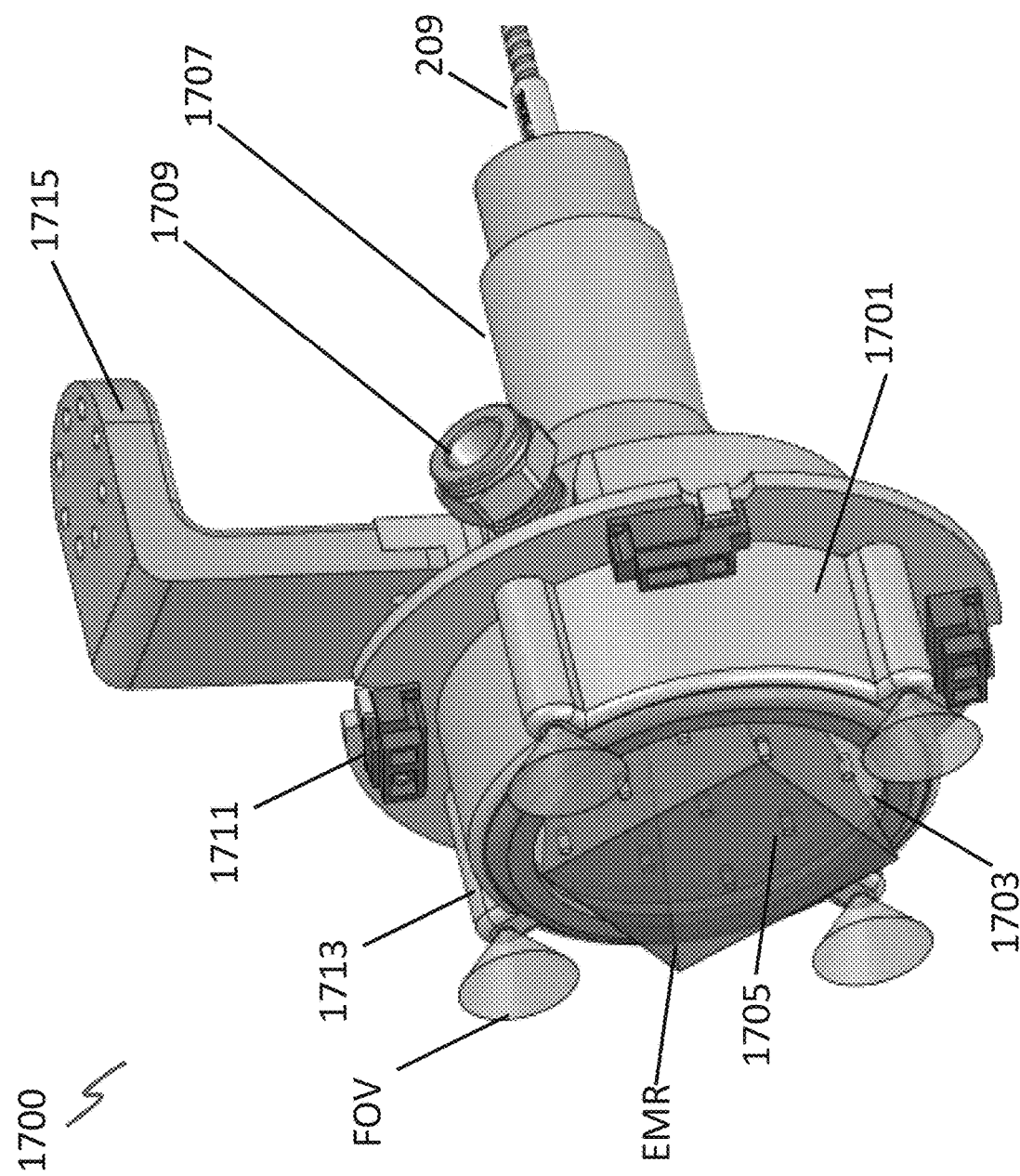
FIG. 17 is a perspective view of a device having non-contact sensors in accordance with an embodiment of the present invention.

Referring now to FIG. 17, a device 1700 is configured for emitting the EMR beam received via the fiber output 209 for treatment of the patient without contacting the treatment area. In particular, the device 1700 can be configured to direct the EMR beam onto the treatment area, direct cooling airflow onto the treatment area, and provide sensor feedback associated with the treatment area to the controller 403 without making contact with the treatment area.

To that end, the device 1700 can include a housing 1701 having a surface 1703 to be directed at a treatment area. In order to retain an appropriate shape for airflow control and withstand stresses and forces associated with operation, the housing 1701, in some embodiments, can be constructed of any suitable material such as metals, plastics, transparent plastics, glass, polycarbonates, polymers, sapphire, any other suitable material, or combinations thereof. To the extent that it is desirable to permit the EMR to be transmitted through the housing 1701 to be directed to the treatment area, it may be advantageous to form at least a portion of the housing 1701, in particular at least a portion of the surface

1703, from an optically transparent material. In some embodiments, the entire housing 1701 can be optically transparent. As shown in FIG. 17, in some embodiments, the housing 1701 may not be optically transparent while the surface 1703 is transparent. However, in general, portions of the surface 1703 proximate to or coincident with the EMR beam should generally be optically transparent so as not to interfere with transmission of the EMR.

To facilitate transmission of the EMR beam therethrough, the housing 1701 can also include an EMR port 1707 for engagement with the fiber output 209 to direct the EMR beam through the housing 1701, including the surface 1703, and onto the treatment area. In accordance with various embodiments, the EMR port 1707 can include any fitting capable of engaging the fiber output 209, such as, for example, a Luer slip, a Luer lock, a fitting, a fiber coupler, or any other suitable fitting. More generally, the EMR port 1707 can include any configuration suitable for directing an EMR beam generated by the fiber output 209 through the housing and toward the treatment area.

In some embodiments, the device 1700 can include beam shaping optics (not shown) for producing a particular beam shape. For example, as shown in FIG. 17, the beam shape can be an expanding square beam. However, although the EMR is shown in FIG. 17 as being an expanding square beam, it will be apparent in view of this disclosure that any other beam shape can be used in accordance with various embodiments, including, for example, expanding, converging, straight, homogenized, collimated, circular, square, rectangular, pentagonal, hexagonal, oval, any other suitable shape, or combinations thereof.

The device 1700, as shown in FIG. 17, can also serve as an air cooling apparatus for cooling the treatment area. To that end, the device 1700 can include one or more cold air ports 1709 for receiving airflow into the housing 1701. Each cold air port 1709 can be any suitable design, size, or shape for connecting to an airflow source, including, for example, an opening in the housing 1701, a tube in fluid communication with the housing, a luer lock connector, a luer slip connector, a fitting, any other suitable design, or combinations thereof. In some embodiments, the cold air port 1709 can be formed integrally with the housing 1701. In some embodiments, the cold air port 1709 can be a separate element attached to, fastened to, or otherwise in fluid communication with the housing 1701.

The airflow received into the housing 1701 via the cold air port 1709 can be directed through the surface 1703 toward the treatment area for direct air cooling of the treatment area. In particular, the surface 1703 can include a plurality of openings 1705 formed in the surface 1703 for directing airflow onto the treatment area. In some embodiments, the openings 1705 can be positioned to direct the airflow onto the treatment area at temperatures, flow rates, and exit flow velocities suitable to maintain the treatment area at a therapeutically acceptable temperature range while avoiding interference with the EMR being directed at the treatment area. To that end, openings 1705 coincident with or within close proximity to a portion of the surface 1703 through which the EMR is transmitted (EMR transmission region) can be formed from optically transparent material. To the extent that other openings 1705 are not aligned with the EMR transmission region, those openings may not need to be transparent.

In some embodiments, the plurality of openings 1705 can be arranged in a pattern that can provide substantially uniform cooling over at least the treatment area illuminated by the EMR. In some embodiments, the substantially uniform cooling can extend over an area larger than the treatment area. In such embodiments, pre and post cooling to the treatment area is permitted as the device 1700 is moved from one treatment area to another by the positioning apparatus 900, whether manually or by automated control by the controller 403 as programmed to deliver the appropriate energy to maintain the target temperature range for a procedure.

In order to promote a uniform flow and maintain a desired cooling rate, during use, the openings 1705 can be spaced apart from the target surface to maintain the substantially uniform cooling and to promote efficient jet impingement cooling. For example, in some embodiments, the spacing between the exit plane of the openings 1705 and the target surface can be maintained between zero (0) inches to more than an inch. In some embodiments, the spacing can be about 0.5 inches. More generally, any spacing between the openings 1705 and the target surface can be used so long as substantially uniform cooling can be provided to the treatment area to maintain a therapeutically acceptable temperature range.

The spacing and positioning of the device 1700 can generally be maintained by adjustment of the positioning apparatus 900 as described above with reference to FIG. 9. To facilitate positioning of the device 1700 by the positioning apparatus 900, the device 1700, in some embodiments, can include a device mount 1715 for operatively engaging the device 1700 with the positioning apparatus 900 (not shown in FIG. 17). For example, as shown in FIG. 17, the device mount 1715 can include a flange for removable engagement with the positioning apparatus 900. However, it will be apparent in view of this disclosure that any device mount 1715 capable of providing removable engagement with the positioning apparatus 900 can be used in accordance with various embodiments.

Although shown in FIG. 17 and described herein as including a device mount 1715 and as being mounted to the positioning apparatus 900, it will be apparent in view of this disclosure that, in some embodiments, the device 1700 may, in some embodiments, be used as a manual hand piece. In such embodiments, the device 1700 may not include a device mount 1715 and instead can be coupled to the housing 100 only by the fiber output 209 at the EMR port and/or a cooling air supply at the cold air port 1709 for permitting manual operation and positioning of the device 1700.

In particular, the spacing can be maintained by providing program instructions for the computing device 107 and the controller 403 for operating the positioning apparatus 900 responsive to real time feedback from one or more position sensors 1711 mounted to the housing 1701 and directed toward the treatment area. The position sensors 1711 can be configured to detect one or more of a distance between the device 1700 and the target area, an orientation of the device 1700 relative to the target area, and a position of the device 1700 on the target area. The position sensors 1711 can generally be any suitable sensor for providing non-contact detection of a position of the device 1700 relative to the target area. For example, as shown in FIG. 17, the position sensors 1711 can be infrared location sensors.

In order to aid in meeting procedure requirements, in some embodiments, the device 1700 can include one or more temperature sensors 1713 to provide real time monitoring of a temperature of the treatment area. In particular, as shown in FIG. 17, the temperature sensors 1713 can include one or more non-contact pyrometers to provide non-contact temperature monitoring of the treatment area. In some embodiments, the temperature sensors 1713 can be configured to provide real time temperature feedback to the computer 107 and/or the controller 403. The computer 107 and/or the controller 403 can then responsively adjust one or more operating parameters of the system 10 to maintain the target area at a therapeutically acceptable temperature. For example, in some embodiments, responsive to the temperature feedback provided by the temperature sensors 1713, the controller 403 can at least one of instruct the positioning apparatus 900 to adjust a spacing between the treatment area and the device 1700, instruct the positioning apparatus 900 to adjust a scanning velocity of the emitted EMR beam relative to the target area, instruct the pump 507 to adjust a flow rate of the cooling air or gas, instruct the refrigeration unit 501 to adjust a coolant temperature, thereby adjusting a temperature of the cooling air or gas, instruct the laser sources 203 to adjust a power of the emitted EMR beam(s), shut off or activate one or more of the laser sources 203, instruct the device 1700 to adjust beam shaping optics to alter a beam shape of the emitted EMR beam, or combinations thereof.

Referring now to FIG. 15, an device 1500 is illustrated wherein the common output cable 209 is split by a beam splitter (not shown) to provide two or more output cables 1501a, 1501b for emitting two or more beams, each delivering only a portion of the total EMR power transmitted by the common output cable 209. Alternatively, in some embodiments, rather than splitting a common output cable 209, the two or more output cables 1501a, 1501b can each be separate, unsplit output cables directly connected to a single laser source 203 and/or the combiner 207. In such embodiments, the array 200 can include a corresponding number of laser sources 203 each having a same wavelength to deliver beams having the same wavelength via each of the emitter cables 1501a, 1501b. Advantageously, such embodiments can permit the use of smaller, lower power, less expensive laser sources 203 because each emitter cable 1501a, 1501b is only required to deliver a portion of the total EMR power used for treatment of the treatment area.

The device 1500 is configured to direct the beams emitted from the output cables 1501a, 1501b at an angle such that the beams impinge separately on a surface to be illuminated S and overlap beneath the surface S in a subsurface tissue to be treated T. Such embodiments can generally provide a lower power density at the point of impingement on the surface S and a higher power density in the overlap region in the tissue T. In particular, power density in the overlap region will scale proportionally with the number of EMR output cables 1501a, 1501b, the power of each EMR beam, and the beam size of each beam in the overlap region. Accordingly, it will be apparent in view of this disclosure that any number of output cables producing any number of EMR beams can be used in accordance with various embodiments as desired to provide a desired power density at the surface S and in the overlap region of the tissue T. For example, in some embodiments, four beams can be provided wherein two pair of opposing beams can be configured in a square arrangement to emit beams at the slant angle to project a rectangular pattern onto the surface S and into the tissue T. In some embodiments, to overlap two more EMR beams from opposing but orthogonal locations, each beam footprint can be rectangular to create a similar projected beam foot print on the treatment plane. More generally, the beam shape of each EMR beam, in some embodiments, can, for example, be diverging, collimated, converging circular, square, rectangular, any other suitable shape, or combinations thereof.

Such a configuration is advantageous because, during, for example, a procedure for hyperthermia of adipose tissue to create apoptosis, the objective is to reach temperatures in the fat (adipose) tissue roughly from 42 to 47° C. During this process where the fat tissue is positioned beneath the skin and epidermis by approximately 2.8 mm, the skin, including the active nerve endings therein, can reach temperatures that feel warm or even hot to the patient. Although cold air or cryogenic cooling is typically provided, higher EMR power densities may nevertheless raise skin temperature to an uncomfortable temperature. In such cases, splitting the EMR power into two or more beams impinging separately on the surface of the skin can reduce local skin heating. On the other hand, the sum power of all overlapping beams is concentrated where the EMR beams overlap. Because maximum power is achieved in the overlap region, higher temperatures can be achieved in the overlap region for more efficient apoptosis. Conversely, the lower power density on the skin, epidermis, and dermis will result in lower temperatures in those regions. In some embodiments, such lower power density can reduce skin cooling requirements for maintaining patient comfort and safety during the treatment.

Additionally, by setting or adjusting beam impingement angle of the beams emitted by the output cables 1501a, 1501b, a depth of tissue treatment can be controlled. In particular, by decreasing the angle of the multiple beams relative to vertical, the overlap region can be formed deeper into the tissue and/or extend deeper into the tissue. Advantageously, by overlapping the beams deeper in the tissue T, more tissue T can be treated during a procedure. Additionally, deeper treatment areas can target different, deeper tissues T than single beam systems or systems having a shallow overlap region. Thus, particular selection or adjustment of slant incident angles, including, for example, from about three (3) degrees to about 75 degrees, can provide high EMR power targeted at a desired depth in the desired tissue T without overheating the impingement surface S.

Figure 16A:
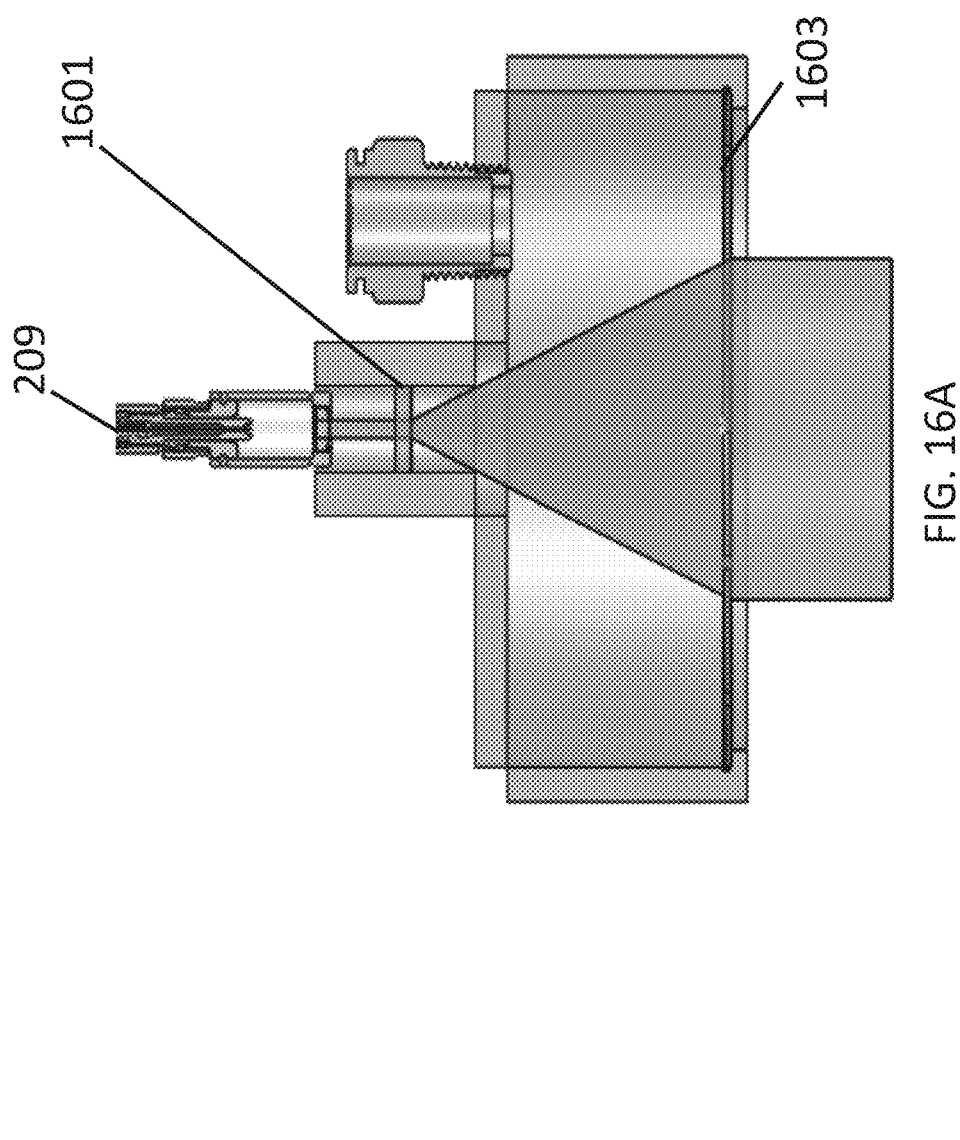
FIG. 16A is a cross-sectional view of a device having beam shaping optics in accordance with an embodiment of the present invention.

Referring now to FIG. 16A, in some embodiments, an device 1600 can include one or more optical elements for expanding, homogenizing, and refocusing EMR energy to aid treatment. In particular, a straight beam directed at a surface S to be illuminated can concentrate the EMR power in a small treatment area, making temperature management difficult and requiring additional movement and time to treat a target tissue T. Thus, in some embodiments, the device 1600 can include a beam expander 1601 to expand a size of a beam emitted by the common output cable 209. In particular, the beam expander 1601 of FIG. 16 is shown as a diffractive optical element (DOE) beam expander 1601. However, it will be apparent in view of this disclosure that any beam homogenizer, beam expander, or combination thereof can be used in accordance with various embodiments.

Figure 16C:
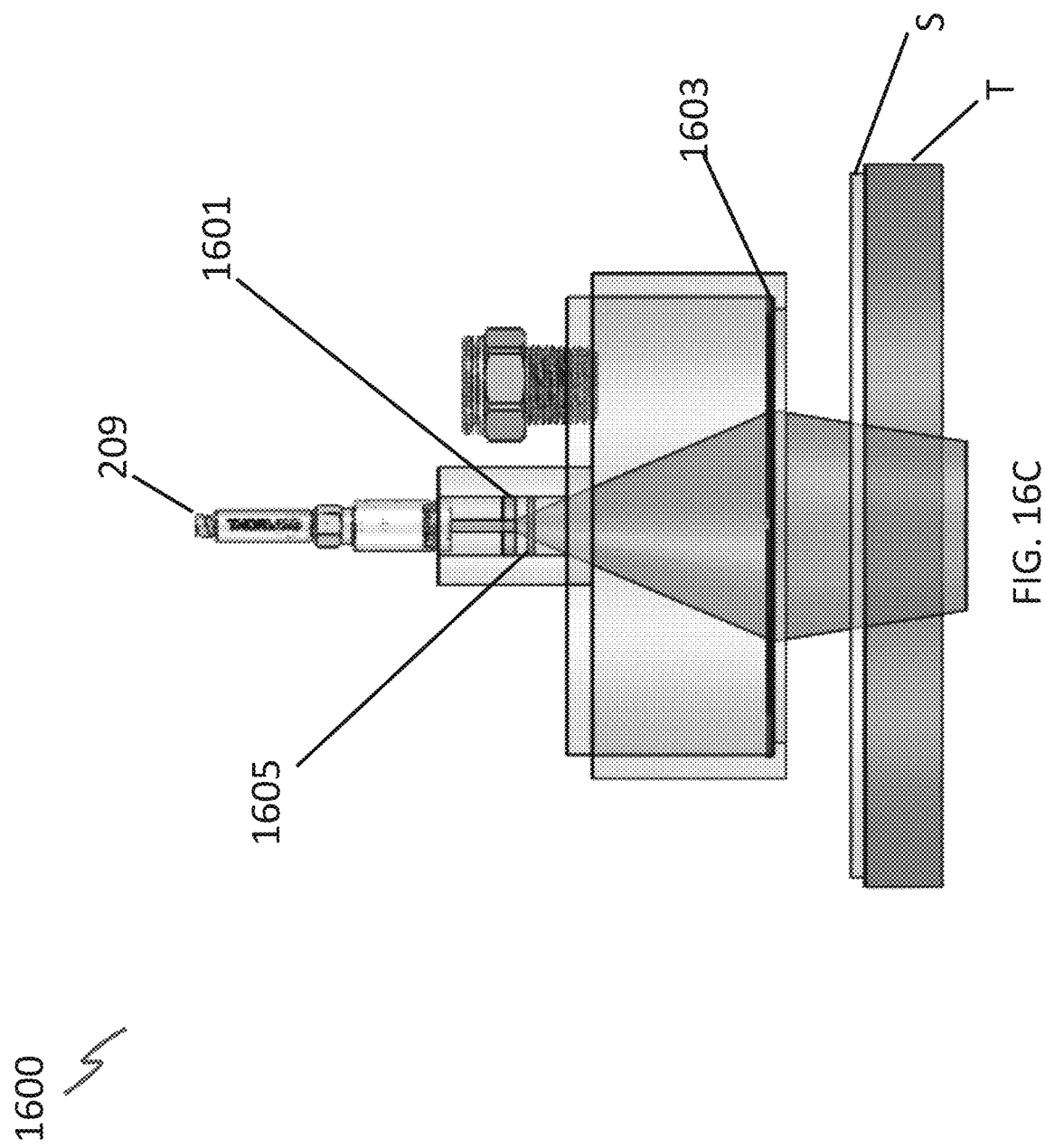
FIG. 16C is a cross-sectional view of the device of FIG. 16A having an additional optical element in accordance with an embodiment of the present invention.

For applications where the target tissue T is beneath a surface S to be illuminated (e.g., where apoptosis of adipose tissue is desired), a beam expander 1601 alone would cause the beam power to be most diffuse in the target tissue T. Such a configuration makes heat management of the illuminated skin more difficult because the skin surface S is exposed to more concentrated beam power and thus heats up more quickly than the target tissue T. Therefore, in some embodiments, the device 1600 can also include a Fresnel objective lens 1603 for refocusing the expanded beam. As shown in FIG. 16B, in some embodiments, adjusting a spacing between the DOE beam expander 1601 and the Fresnel objective lens 1603 can adjust the focus. Thus, in some embodiments, the beam can be adjusted to be narrower (more concentrated) in the target tissue T and more diffuse at the surface S such that the skin surface S heats more slowly than the target tissue T. Referring now to FIG. 16C, in some embodiments, a negative Fresnel lens 1605 can be positioned between the beam expander 1601 and the Fresnel lens 1603 to permit additional beam shaping.

Referring again to FIG. 1, the system 10, in some embodiments, can include one or more sensors 1000 for monitoring operational conditions such as temperature of the treatment area. In some embodiments, the sensors 1000 can be configured to provide real time feedback to the computing device 107 so that the computing device 107 can, if desired, provide instructions to one or more components of the system 10 to alter one or more operational properties of the system 10 in response to the feedback. For example, in some embodiments, the positioning apparatus 900 can be instructed to scan the target area faster or slower to decrease or increase dwell time, move the device 950 closer to or further away from the target surface, reposition the device 950, temporarily suspend treatment, terminate treatment, increase or decrease cooling flow through a patient cooling system.

To the extent that patient temperature data is required, in some embodiments, to maintain a therapeutically acceptable temperature range, a subcutaneous temperature prediction sensor 1000 can be provided. By way of background, various tools and methods in the prior art have tried to non-invasively measure core or fat temperatures in the human body. Some rely on blackbody radiation signals in the microwave region. Others employ temperature sensors, in combination with estimated skin and tissue thermal conductivity, to predict the core temperature. These types of devices are too large, complicated or expensive to be applied to normal aesthetic treatment settings. Some devices have attached heated sensors to the skin with temperature sensors to predict core temperatures. Other approaches have monitored the skin surface temperature and the energy input.

Invasive temperature measurements are possible but not preferred due to the associated risks, and desire for a fully non-invasive hyperthermia treatment. Elaborate instruments such as MRI (Magnetic Resonance Imaging) or advance ultrasonic devices are capable of these measurements, but involve expensive and large devices which are also not readily used during many treatments.

A non-invasive sensor 1000 for measuring a core body fat temperature of a patient, the sensor 1000 can include a temperature sensor 1001 for measuring skin surface temperature and a heat flux sensor 1003 for measuring heat flow into or out of the treatment site. In some embodiments, the temperature sensor 1001 can include, for example, a thermocouple or a non-contact pyrometer. In some embodiments, the heat flux sensor 1003 can include, for example, a thermopile or a Seebeck effect sensor.

The sensor 1000 can then continuously monitor temperature and heat flux of the patient during treatment and feed that data back to the computing device 107 for processing. The temperature and heat flux data can be synthesized in an algorithm with user input data such as patient skin type, age, size, body fat percentage, etc. to estimate a temperature of the target subcutaneous fat. The computer system 107 can then adjust one or more operating parameters such as pulse length, EMR source activation, EMR source power, treatment duration, cooling airflow, scanning speed of the positioning apparatus, etc. to manage the temperature in response to the sensor 1000 feedback. Although shown as including both a temperature sensor 1001 and a heat flux sensor 1003, it will be apparent in view of this disclosure that, in some embodiments, the sensors 1000 may include only a temperature sensor 1001 or only a heat flux sensor 1003.

In some embodiments, the continuous temperature monitoring can begin with a numerical finite element simulation of fat region heating under EMR illumination to predict temperature over time and EMR source modulation. In particular, EMR source heating is applied in time dependent modulation and diminishes with depth of penetration. As the procedure progresses, skin temperature and skin heat flux are measured for the patient using the temperature sensor 1001 and the heat flux sensor 1003. Then, the temperature and heat flux data, the patient's unique data, and the finite element model are entered and combined in an overall algorithm to control the radiation input actively and maintain fat temperature in the effective range.

The measured parameters of a patient's skin temperature and skin heat flux in cooled regions can be measured several ways. Skin surface temperature can be made by a non-contact optical pyrometer recording in the radiated region, or a thermistor or thermocouple package. Temperature will be monitored before, during, and after EMR source irradiation. The rate of change of the skin temperature is monitored in the algorithm. The skin heat flux is derived in a non-contact method using the surface temperature measurement in combination with actively monitored cooling flow rate. When the two measurements are included in a heat transfer algorithm, calculation of skin heat flux is possible. Alternatively, a surface heat flux sensor can provide heat flux data.

Patient data used in this algorithm includes skin type and pigment, gender, age, size, weight, body mass index, and possible pretreatment history and skin distinctions. When available, more detailed tissue data can be entered. Tissue profiling collected from MRI's or ultrasonic devices can also provide accurate parameters to be incorporated into the tissue model. Other technologies such as non-invasive body core temperature measurement instruments that use black body radiation in the microwave region can be applied. Patient factors such as skin pigment characterization are important to estimate the anticipated EMR transmission and absorption values.

The algorithm is used to control the EMR energy delivered to a treatment area, known as fluence, in watts per square centimeter, as well as the exposure durations. The hyperthermia adipose reduction is normally done with on-off modulations and possible movement of beam location, which returns to reheat a region to maintain effective temperature range. The skin cooling is expected to be controlled based on skin surface temperature feedback for comfort level (e.g. 30° C.) and maximum safe temperature (e.g. 40° C.). The entire treatment period can last from several minutes to more than 30 minutes.

Figure 12:
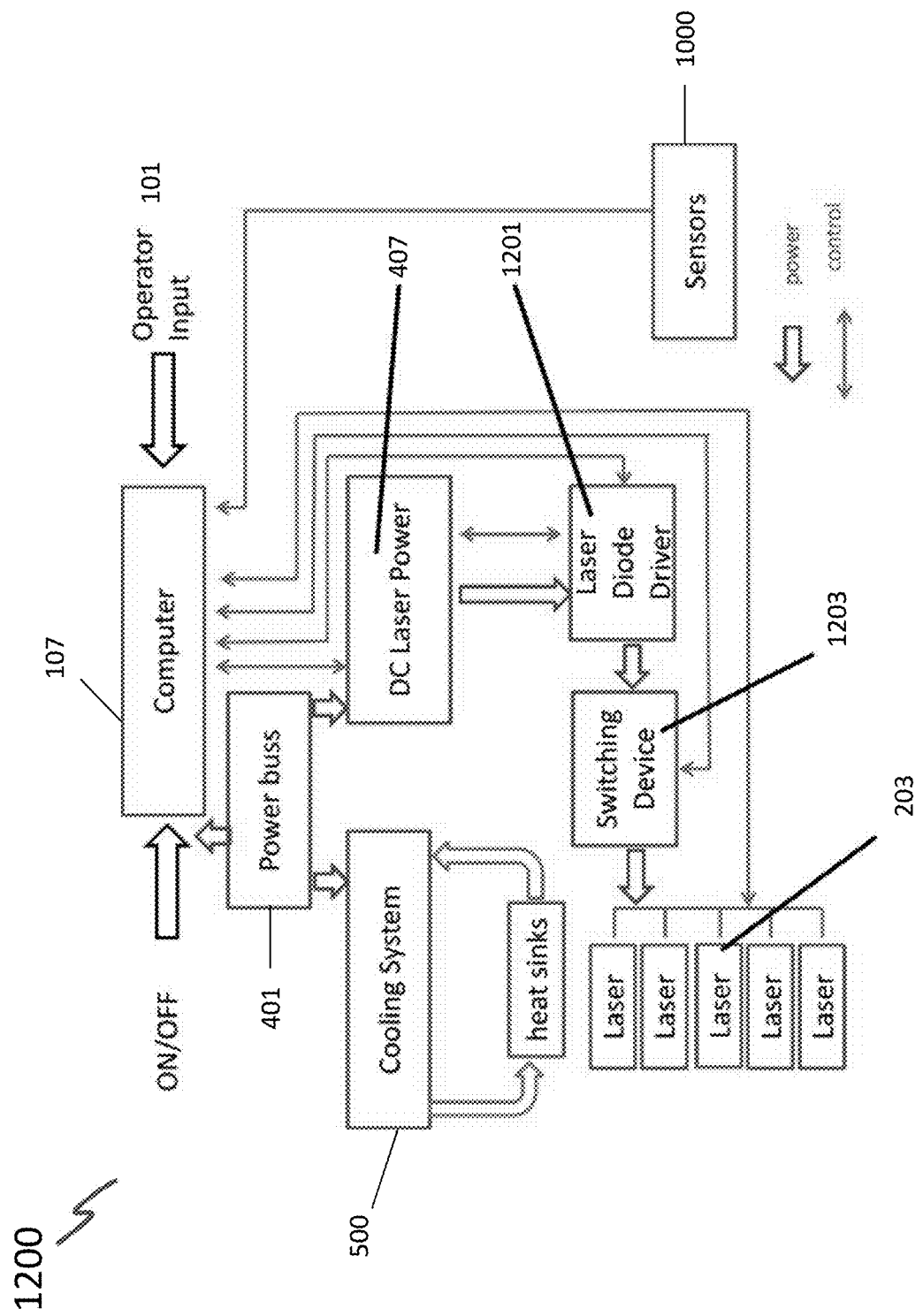
FIG. 12 is a schematic view of a multifunction system including a switching device in accordance with an embodiment of the present invention.

Referring now to FIG. 12, a schematic of a system 1200 for electronics and control of a multifunction aesthetic system having a single diode driver is provided. In particular, the high voltage ADC 411 can operate several laser sources 203 from a shared diode driver module. In this case, multiple laser sources 203 of the same voltage/current requirements are operated from a single diode driver. In some embodiments, the system 1200 is substantially similar to the system 400 of FIG. 4. However, the system 1200 of FIG. 12, includes a single diode driver 1201 and a switching device 1203 interposed between the diode driver 1201 and the laser sources 203 to permit the diode driver 1201 to selectively drive a desired one of the laser sources 203.

The diode driver 1201, in some embodiments, can be substantially similar to the diode drivers 409 discussed above in connection with FIG. 4. The switching device 1203, in some embodiments, can be configured to switch the driver 1201 between the diode load of each laser source 203 as required. In some embodiments, the switching device 1201 can include one or more high current mechanical relays, one or more solid state relays (SSR), or both.

The switching device 1203 can be placed on 'high side' of the diode driver and the relays can be selected one at a time to drive a particular laser source 203. The relays must be capable of handling the current driven to the selected laser source 203. The relays or SSRs can be used as a safety interlock (emergency power cut) for the laser sources 203 as well. However, in the configuration of FIG. 12, multiple laser sources 203 cannot be driven by selecting more than one relay at a time. Such a configuration would place the laser sources 203 in parallel with each other and the driver 1201. Even if the driver 1201 is capable of sufficient current, there is no passive or active load sharing between the two laser sources 203. Because one of the diodes will have a lower resistance, that device will 'hog' the current, over power, and burn out, leaving the second channel to do the same. Because such burnout can happen very quickly (seconds), the switching device 1203 must be configured to select only one diode at a time. Additionally, switching the diode channel must occur when the driver is off. In particular, diode laser sources 203 operate at a near short (about 3 milliohms for a diode bar). Therefore, if the output of an active driver is switched from an open load to a diode load, a large overcurrent spike will occur, likely damaging or destroying the diode.

When deciding between SSR and mechanical relays, SSRs tend to be faster, more reliable, and don't typically require electrically isolated control lines. However, isolated input SSRs allow the use of a single driver for several diodes with less concern for ground loop issues. In addition, in the event of a failure, an isolated SSR input will provide a buffer for the sensitive control circuitry.

Figure 13:
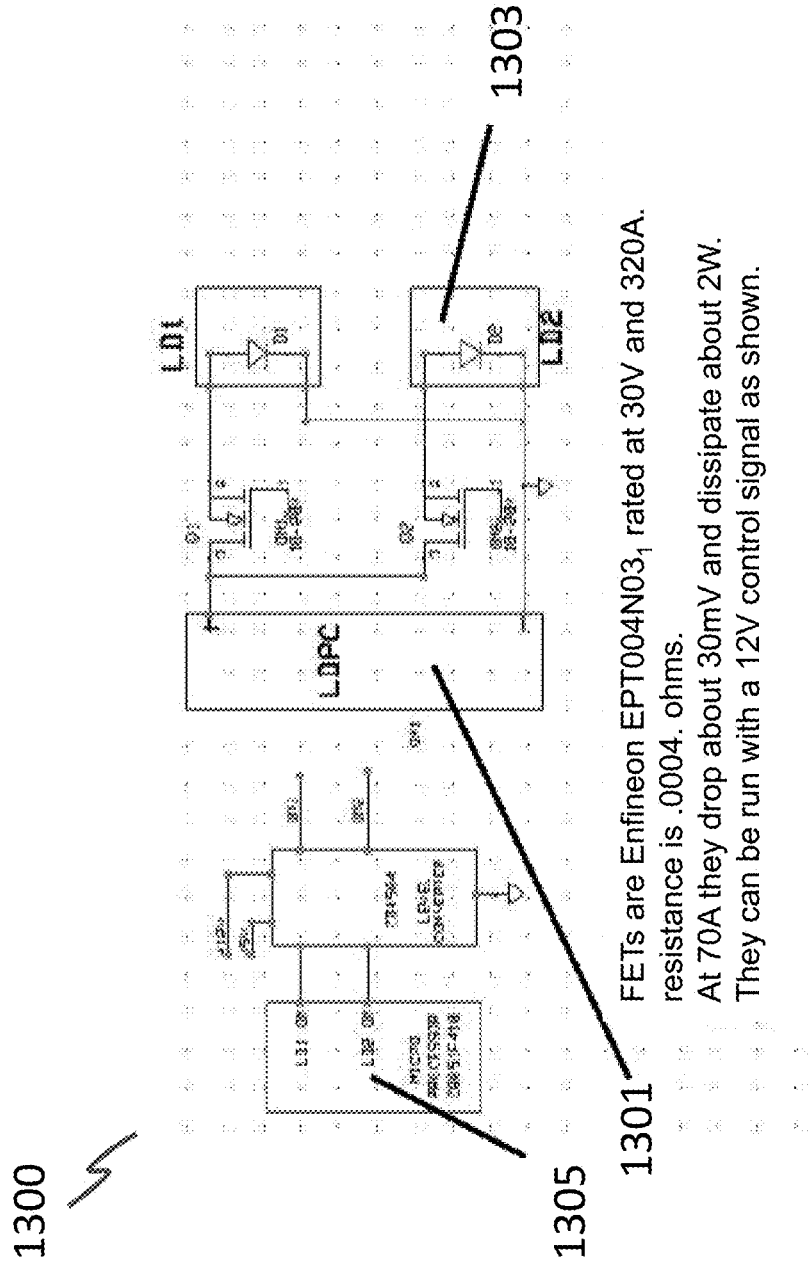
FIG. 13 is a schematic view of a FET circuit of a switching device in accordance with an embodiment of the present invention.

Referring now to FIG. 13, in some embodiments, the switching device can employ a single Diode Driver Printed Circuit (DPC) 1301 to power multiple EMR sources 1303 is shown. The high current capacity FET's can be used as switching devices to activate and power the selected EMR source. This diagram shows only two drivers (LD1 and LD2), but the same concept can be applied to drive multiple EMR sources. The control input to the switching FET's is routed from the processor 1305. This design approach eliminates the need for switching relays with the command signal driving only the selected driver and therefore activating that EMR source.

Example Embodiment

Figure 11:
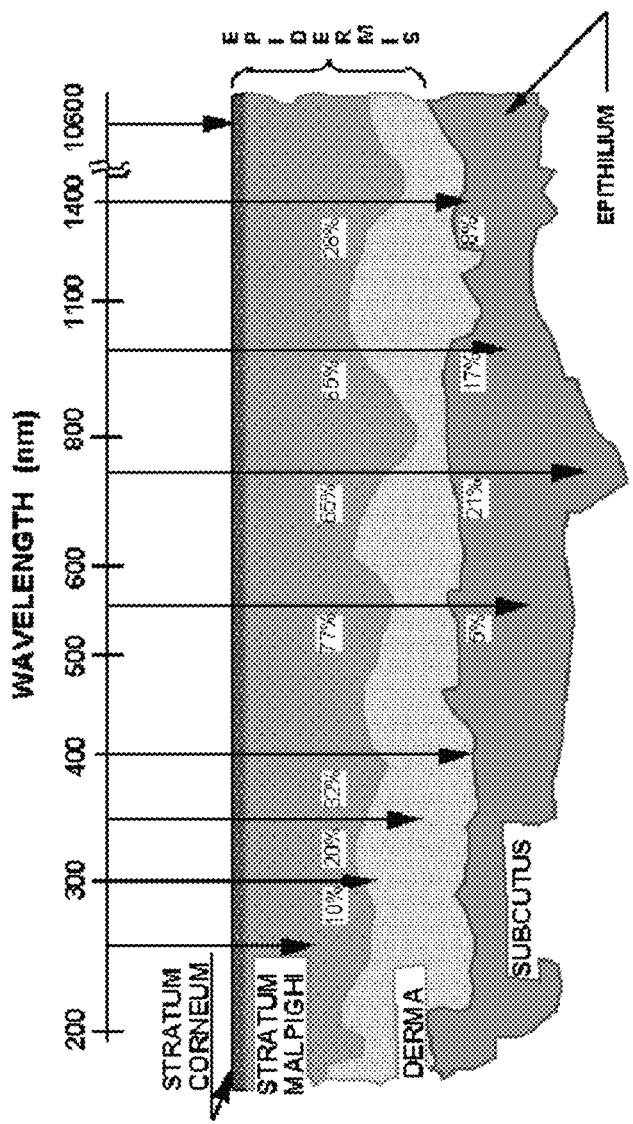
FIG. 11 is a human tissue profile showing expected penetration depth of various EMR wavelengths in accordance with an embodiment of the present invention.

In one embodiment, it may be desirable to perform subcutaneous fat reduction and skin tightening simultaneously. However, as shown in the human tissue profile of FIG. 11, different EMR wavelengths have different expected penetration depths. In particular, FIG. 11 illustrates, by percentage, for each wavelength, the percentage of EMR energy penetrating to various depths. More generally the fat is typically more than 5 mm from the skin's surface. Thus, for example, a wavelength of about 1064 nm (e.g., 400 nm to 3000 nm or 900 nm to 1100 nm) can be selected for hyperthermia of fat tissue because it exhibits good transmission through the skin, epidermis, and dermis and deposits its energy within the fat cells. On the other hand, skin tightening generally requires other wavelengths that exhibit higher absorption in the epidermis and dermis, where the collagen resides. Thus, for example, a wavelength of about 400 nm to about 3000 nm or about 1300 nm to about 1400 nm. These EMR beam wavelengths deposit more energy to the collagen, creating necrosis and eventually skin tightening from new collagen regrowth.

In such an embodiment, the controller 403 of the power and control electronics 400 of the multifunction aesthetic system 10 described herein can activate a first driver 409/laser source 203 pair to produce an EMR beam having a wavelength suitable for subcutaneous fat reduction while simultaneously activating a second driver 409/laser source 203 pair to produce an EMR beam having a wavelength suitable for skin tightening. In some embodiments, such a procedure can also be used in conjunction with other fat reduction techniques such as procedures using RF (radio frequency), MW (microwave), ultrasonic, or cryo (cold therapy) fat reduction methods.

In further example, in some embodiments, the methods described above can be used to activate driver 409/laser source 203 pairs for emitting wavelengths suitable for performing any other procedure or combination of procedures including, for example, but not limited to, fat reduction, body skin tightening, facial skin tightening, skin resurfacing, skin remodeling, vein reduction or removal, facial pigment removal or reduction, hair removal, acne treatment, scar reduction and removal, psoriasis treatment, stretch mark removal, nail fungus treatment, leukoderma treatment, tattoo removal, or combinations thereof as discussed above.

While the present disclosure has been described with reference to certain embodiments thereof, it should be understood by those skilled in the art that various changes may be made and equivalents may be substituted without departing from the true spirit and scope of the disclosure. In addition, many modifications may be made to adapt to a particular situation, indication, material and composition of matter, process step or steps, without departing from the spirit and scope of the present disclosure. All such modifications are intended to be within the scope of the claims appended hereto.

What is claimed is:

1. A system for producing hyperthermia of adipose tissue comprising:
    an energy source for directing energy suitable for producing hyperthermia in adipose tissue at a treatment region;
    a positioning apparatus for moving the energy source over the treatment region; and
    a temperature sensor to provide feedback data from the treatment region, so that movement of the energy source by the positioning apparatus can be controlled to maintain a target temperature range conducive for creating apoptosis in adipose tissue at the treatment region.

2. The system of claim 1, wherein the temperature sensor provides feedback to a computer to allow the computer to control movement of the positioning apparatus to control the energy delivery.

3. The system of claim 1, wherein the positioning apparatus comprises a robotic arm having a treatment device housing the energy source which directs the energy to the treatment region.

4. The system of claim 3, wherein the housing further comprises one or more ports for the delivery of a cooling airflow impinging on a surface of the treatment region.

5. The system of claim 4, wherein the housing further comprises an optical element for modifying the energy beam and to direct the energy beam onto an expanded treatment region.

6. The system of claim 1, wherein the target temperature range is between 40° and 48° C.

7. The system of claim 6, wherein the temperature sensor reads a temperature of skin at a surface of the treatment region.

8. The system of claim 6, wherein a computer adjusts at least one operating condition of the energy in response to the temperature feedback when a temperature of skin at the treatment site exceeds a maximum safe temperature.

9. The system of claim 8, wherein the at least one operating condition is at least one of moving the positioning apparatus for delivery of energy to a second treatment region, adjusting a flow rate of a cooling airflow impinging on the treatment region, adjusting a temperature of the cooling airflow impinging on the treatment region, adjusting a spacing between the treatment region and a cooling apparatus directing the cooling airflow onto the treatment region, a adjusting power of the energy, adjusting a scanning speed of the energy relative to the treatment region, or combinations thereof.

10. A multifunctional aesthetic system comprising:
a source for directing an electromagnetic radiation (EMR) beam to a treatment region having adipose tissue;
a controller in electronic communication with the source; and
a temperature sensor in electronic communication with the controller for providing feedback data from the treatment region to the controller to adjust at least one operating condition of the EMR beam in response to the feedback data; and
a positioning apparatus for providing movement of the source, the positioning apparatus in electronic communication with the controller for instructing movement of the positioning apparatus such that the EMR beam is emitted from the source onto the treatment region to maintain a target temperature range conducive for creating apoptosis in adipose tissue at the treatment region.

11. The system of claim 10, further comprising a housing coupled to the positioning apparatus, the housing having one or more ports for the delivery of a cooling airflow impinging on the treatment region.

12. The system of claim 11, wherein the temperature sensor is located in the housing.

13. The system of claim 10, further comprising a position sensor in electronic communication with the controller for maintaining the source a set distance above the treatment region.

14. The system of claim 10, wherein the at least one operating condition is at least one of moving the positioning apparatus for delivery of energy to a second treatment region, adjusting a flow rate of a cooling airflow impinging on the treatment region, adjusting a temperature of the cooling airflow impinging on the treatment region, adjusting a spacing between the treatment region and a cooling apparatus directing the cooling airflow onto the treatment region, a adjusting power of the energy, adjusting a scanning speed of the energy relative to the treatment region, or combinations thereof.

15. A multifunctional aesthetic system comprising:
a source for directing an electromagnetic radiation (EMR) beam to a treatment region;
a controller in electronic communication with the EMR source to direct the EMR beam to a treatment region having adipose tissue, wherein a total area of the treatment region is larger than an area of the EMR beam incident on the treatment region; and
wherein the controller directs movement of the EMR source in a pattern that encompasses the total area of the treatment region with a speed sufficient to allow the adipose tissue to be maintained within a therapeutically acceptable temperature range to create apoptosis.

16. The system of claim 15, further comprising a temperature sensor in electronic communication with the controller for providing feedback to the controller.

17. The system of claim 15, further comprising a position sensor in electronic communication with the controller for maintaining the EMR emitter a set distance above the treatment region.

18. The system of claim 15, further comprising a positioning apparatus for movement of the EMR source over the treatment region, wherein the controller controls the movement of the positioning apparatus such that the EMR beam is emitted from the EMR source onto the treatment region.

19. The system of claim 18, further comprising a housing coupled to the positioning apparatus, the housing having one or more ports for the delivery of a cooling airflow impinging on the treatment region.

* * * * *